United States Patent
Szu et al.

(10) Patent No.: US 7,366,564 B2
(45) Date of Patent: Apr. 29, 2008

(54) NONLINEAR BLIND DEMIXING OF SINGLE PIXEL UNDERLYING RADIATION SOURCES AND DIGITAL SPECTRUM LOCAL THERMOMETER

(75) Inventors: Harold H. Szu, Bethesda, MD (US); James R. Buss, Arlington, VA (US); Ivica Kopriva, Washington, DC (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 707 days.

(21) Appl. No.: 10/652,086

(22) Filed: Aug. 22, 2003

(65) Prior Publication Data

US 2004/0181375 A1    Sep. 16, 2004

Related U.S. Application Data

(60) Provisional application No. 60/405,327, filed on Aug. 23, 2002.

(51) Int. Cl.
 A61B 6/00    (2006.01)
(52) U.S. Cl. ...................... 600/473; 600/474
(58) Field of Classification Search ............... 600/473, 600/479, 309–344, 407, 480
 See application file for complete search history.

(56) References Cited

U.S. PATENT DOCUMENTS 4,718,417 A * 1/1988 Kittrell et al. ................. 606/7
4,723,843 A    2/1988 Zobel
5,339,818 A    8/1994 Baker et al.
5,383,164 A    1/1995 Sejnowski et al.
5,539,832 A    7/1996 Weinstein et al.
5,553,616 A * 9/1996 Ham et al. ................. 600/316

(Continued)

FOREIGN PATENT DOCUMENTS

WO    WO99/66638    12/1999

OTHER PUBLICATIONS

U.S. Appl. No. 60/405,327, filed Aug. 23, 2002, Harold Szu et al.

(Continued)

Primary Examiner—Eleni Mantis-Mercader
Assistant Examiner—John F. Ramirez
(74) Attorney, Agent, or Firm—Gerhard W. Thielma, Esq.; Scott R. Boalick, Esq.; Matthew J. Bussan, Esq.

(57) ABSTRACT

Changes, increase or decrease, in the body fluid flow are passively detected by using a single pixel, non-linear blind de-mixing procedure, which can be extended to general biomedical measurement and diagnoses instruments. More specifically the single pixel, non-linear blind de-mixing procedure is applied on the hot spots of rheumatic arthritis or breast cancer detection problem using passive two-color infrared imaging as well as to passively detect blockages in the body fluid circulatory system that might be of importance for coronary artery bypass surgery, diabetes and deep vein thrombosis. Other applications of the mentioned algorithm include a pair of cameras for video, a pair of antennas for cell phones, and in situ data gathering or imaging using multiple mode fiberoptical sensing as well as selective amplification hearing aids through two-ear binaural processing for de-noise echo cancellation and signal classification.

10 Claims, 30 Drawing Sheets

U.S. PATENT DOCUMENTS

| | | |
|---|---|---|
| 5,579,778 A | 12/1996 | Baker et al. |
| 5,590,665 A | 1/1997 | Kanai |
| 5,706,402 A * | 1/1998 | Bell .......................... 706/22 |
| 5,746,698 A | 5/1998 | Bos et al. |
| 5,839,438 A | 11/1998 | Graettinger et al. |
| 5,909,646 A | 6/1999 | Deville |
| 5,959,966 A | 9/1999 | Torkkola |
| 6,134,003 A | 10/2000 | Tearney et al. |
| 6,152,879 A | 11/2000 | Mohler |
| 6,185,309 B1 | 2/2001 | Attias |
| 6,186,955 B1 | 2/2001 | Baura |
| 6,294,775 B1 | 9/2001 | Seibel et al. |
| 6,321,111 B1 | 11/2001 | Perelman et al. |
| 6,321,200 B1 | 11/2001 | Casey |
| 6,322,521 B1 | 11/2001 | Hou |
| 6,343,268 B1 | 1/2002 | Balan et al. |
| 6,351,711 B1 | 2/2002 | Chansarkar |
| 6,403,944 B1 | 6/2002 | MacKenzie et al. |
| 6,424,960 B1 | 7/2002 | Lee et al. |
| 6,478,744 B2 | 11/2002 | Mohler |
| 6,480,615 B1 | 11/2002 | Sun et al. |
| 6,539,304 B1 | 3/2003 | Chansarkar |
| 2001/0016682 A1 | 8/2001 | Berner et al. |
| 2001/0016689 A1 | 8/2001 | Heikkila et al. |
| 2002/0099286 A1 | 7/2002 | Sandler et al. |
| 2003/0010898 A1 | 1/2003 | MacKenzie et al. |
| 2003/0036689 A1 | 2/2003 | Diab et al. |

OTHER PUBLICATIONS

Draft of "Homeostasis Theory of Unsupervised Learning", Harold Szu, 6 pages.

A Press Release from the Department of the Navy (http://www.onr.navy.mil) entitled "Detecting Breast Cancer with a New Algorithm", dated Sep. 4, 2002, 2 pages.

* cited by examiner

300

700

800

900

Figure 10A
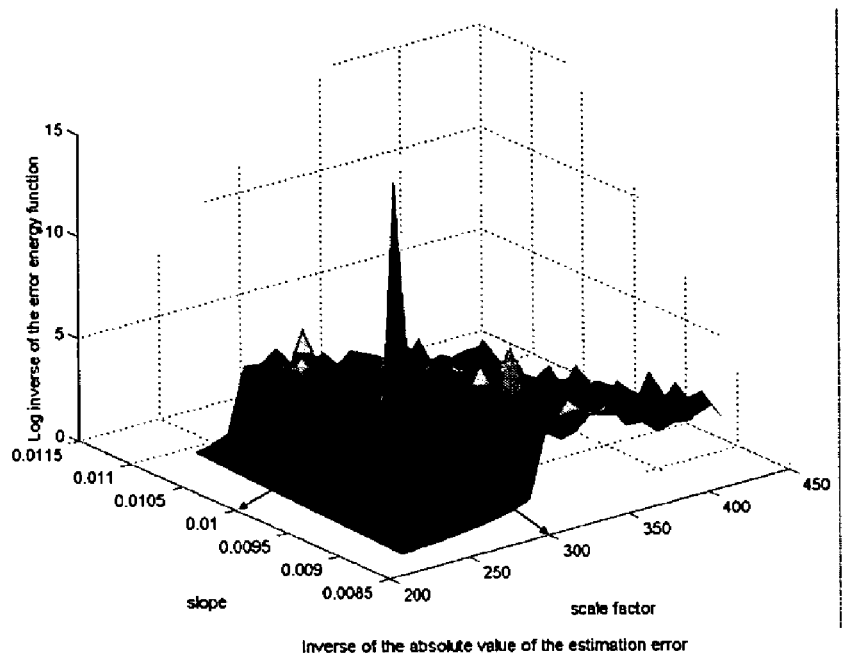
1002
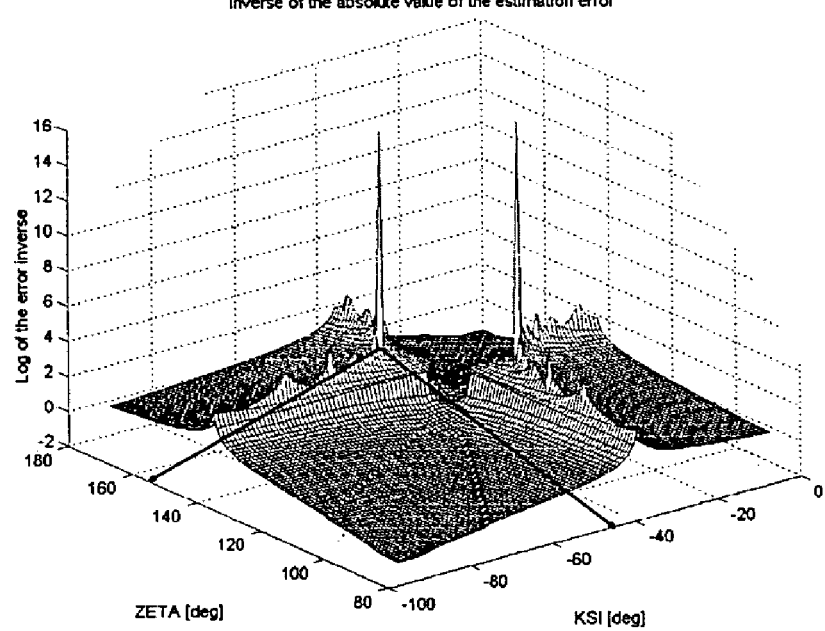
1004
FIGURE 10B

1300

1400

1600

1700

Unmixing matrix [W] adaptation:

1.) SW1 = Opened (O), $\mu_i$ input; no $s_i$ input; no data $x_j$ input;

2.) SW1=Closed (C), data $x_j$ input; no source $s_i$ input; no $\mu_i$ input.

$$x_j \to \mu_i x_j$$

3.) Update unmixing matrix [W] locally:

$$w_{ij} = w_{ij} - \eta \mu_i x_j$$

4.) SW1=C, data $x_j$ input; no source $s_i$ input; no $\mu_i$ input.

$$x_j \to \sum_{j=1}^{N} w_{ij} x_j$$

5.) SW1=C, compute locally at $s_i$ node:

$$\Delta\mu_i = \left(\frac{K_B T_0}{s_i^{(k)}} + \mu_i^{(k)}\right)\left(\vec{w}_i^{(l)} g^{-1}(\vec{X}) - N^{(l)} s_i^{(k)}\right) + \sum_{\substack{j=1\\j\neq i}}^{M} \mu_j^{(k)} \left(\vec{w}_j^{(l)} g^{-1}(\vec{X}) - N^{(l)} s_j^{(k)}\right)$$

$$\mu_i = \mu_i + \Delta\mu_i$$

Source vector $\vec{s}$ adaptation:

6.) Compute partition function $Z$ $$Z = \sum_{k=1}^{M} \exp\left(\frac{1}{kT_0} \mu_k\right)$$

7.) Compute locally source components $s_i$:

$$s_i = \exp(\frac{1}{K_B T_0} \mu_i) / \sum_{k=1}^{M} \exp\left(\frac{1}{K_B T_0} \mu_k\right)$$

$$= \frac{1}{1 + \sum_{\substack{k=1\\k\neq i}}^{M} \exp\left[\frac{1}{K_B T_0}(\mu_k - \mu_i)\right]} = \sigma_i(\vec{\mu})$$

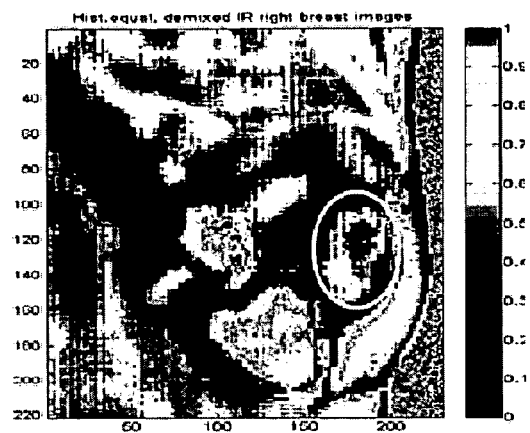
3002
Figure 30A
3004
FIGURE 30B.

NONLINEAR BLIND DEMIXING OF SINGLE PIXEL UNDERLYING RADIATION SOURCES AND DIGITAL SPECTRUM LOCAL THERMOMETER

CROSS-REFERENCE TO RELATED APPLICATIONS

This application is related to, and claims the benefit of priority to, U.S. Provisional Application No. 60/405,327, filed Aug. 23, 2002, entitled *Method and Device for Passive Detection of Changes in Blood Flow by Use of Sensor Pairs Smart Processing System*, by Harold Szu, James Buss, and Ivica Kopriva, the contents of which are incorporated herein by reference.

STATEMENT OF GOVERNMENT INTEREST

The invention described herein was made in the performance of official duties by employees of the Department of the Navy and, thus, the invention disclosed herein may be manufactured, used, licensed by or for the Government for governmental purposes without the payment of any royalties thereon.

BACKGROUND OF THE INVENTION

1. Field of the Invention

The present invention can blindly de-mix a single pixel of underlying unknown sources cases whether the sources are generated by associated heat of warm blood supply needed for a rapid growth of tumor or artificially induced by molecular tagging of fluorescence proteins; and whether the spectrum is infrared radiation, visible fluorescence or invisible Tera-Hertz radio frequency, which are all by definition unknown sources to be identically treated using statistical-mechanics paradigm.

2. Description of the Related Art

Tumor identification based on algorithms (or procedures) using multiple-pixel statistics assuming that a tumor is larger than a pixel is known in the art. More particularly, a statistical, multiple pixel, blind source separation algorithm (procedure), termed ICA (Independent Component Analysis), is known in the art and is based on the factorization of joint probability density. However, these algorithms require that a tumor has reached sufficient size, that is, larger than a pixel, so that its neighborhood can contribute to the determination of the identical mixing matrix [A] shared by all pixels without more unknowns as in the opposite limit of a small tumor having the space-variant [A] for different pixels. In other words, an image of the tumor spreads across at least several neighborhood pixels having similar mixing matrix before the tumor can be identified.

That is, other statistical Independent Component Analyses (ICA) methodologies suffer pixel-averaging blurring effects since the average over neighborhood pixels must implicitly assume an identical breast-medium heat transfer matrix MTF [A] for the space-invariant imaging. This would be true only for a large tumor requiring no earlier target detection.

It would be more desirable to detect a tumor as early as possible in the life cycle of the tumor, before the tumor has reached sufficient size to spread across more than one pixel.

Standard Blind Source Separation (BSS) is known in the art, and is referred to as "Bell-Sejnowski, Amari, and Oja (BSAO)" 4 groups of researchers. "BSAO" has addressed the linear version of BSS. "BSAO" assumed the identical mixing matrix for all pixels using the Artificial Neural Network (ANN) as all pixel data post-processing collectively in order to factorize the joint-probability density function of all pixels known mathematically as the Independent Component Analysis (ICA).

The BSAO ICA unsupervised learning methodology searches for the natural gradient of Artificial Neural Networks (ANN) post-processing weight matrix [W] by means of a typical contrast function: Maximum Entropy (MaxEnt) of integral version of the neurons' outputs:

$$\frac{\partial[W]}{\partial t} = \left\langle \frac{\partial H(\vec{y}([W]\vec{x}))}{\partial[W]}[W]^T[W] \right\rangle_{pixels\,\vec{x}}$$

where BSAO's H is the Shannon entropy S.

of which the natural gradient Riemannian metric of the data distance followed from the Euclidean distance of the neuron output $(\vec{y},\vec{y}) = (\vec{x}, [W]^T[W]\vec{x})$, as shown in FIG. 1.

FIG. 1 is an illustration of the "BSAO", MaxEnt Neural Network 100 of the related art which implements natural gradient based unsupervised learning methodology searching for the post-processing weight matrix [W] by means of a typical contrast function: Maximum Entropy (MaxEnt) of integral version of the neuron's output.

The MaxEnt Neural Network 100 used the pixel ensemble average for the stochastic gradient assuming the same mixing matrix [A] for all the pixels and was consequently non-real-time batch mode algorithm. In multispectral imaging applications (remote sensing, breast cancer detection, fiberoptic data gathering in tissue) the ensemble average property will cause a loss of details that in some cases (breast cancer detection, detection of small objects in the remote sensing) could be unacceptable.

In addition, a single-pixel, remote-sensing ad hoc method, a feedback, linear, Lagrange Constraint Neural Network, by H. Szu is known in the art. This method is based on a gradient descent (or slope) method and is applicable to the far-field radiation linear problems only.

However, real world applications are mostly nonlinear or pseudo-linear.

FIG. 2 shows a single color (short, mid or long IR) breast imaging system 200, which includes single cameras 202 for each of the spectrum colors each of which has different optical axis, and a computer 204 executing a single color infra-red (IR) breast image processing and classification procedure known in the art. Infrared (IR) breast imagining of the related art is based on a single integrated spectral band on either the long (8-12 μm), the mid (3-4 μm), or short IR (1-3μ), shown in FIG. 2, but not on all simultaneously capable for fusion and self-classification.

FIG. 3 is optical layout of a single-mode fiberoptic endoscope 300 of the related art. In situ fiberoptical data gathering or imaging devices of the related art are based on single mode of optical sensing, an example of which is shown in FIG. 3. In the single-mode fiberoptic endoscope 300, light reflected from tissue 302 is directed by objective lens 304 into the single-mode fiber relay 306 to ocular lens 308 and to detector array 301 which detects light of only a single wavelength.

FIG. 4 is a single ear based selective amplification hearing system 400, in which signal+noise is transmitted by detector 402 to a PDA-like device 404 which is transmitted to an earpiece 406. By using a single sensor (one ear) 402 system it becomes more difficult to cancel the noise or interference.

Selective amplification hearing aids 400 of the related art are based on a single inner ear cochlear mechanism, as shown in FIG. 4.

Thermal breast scanning has been employed for a number of years, especially in Europe and Asia, but its use has been limited to a single integrated infra-red band, using a single camera and compared in a chill room about ten minutes the differential cooling rate of malign and benign tumor. Unfortunately, this procedure has generated too much variability to be reliable and reproducible.

In addition, supervised algorithms are known in the art. In supervised algorithms, a standard library is needed but each person is unique in tumor development and personal response physiology that a supervised library approach will create a biased estimation.

Further, trained, supervised neural networks used for medical applications are known in the art. Supervised networks have the limitation of requiring another method of accurately determining the value of the parameter under different conditions. Further, the accuracy of supervised networks is dependent upon the amount of such available "training".

An unsupervised learning process separating unknown source signals with both mixture characteristics and original sources unknown, but using independent component analysis (ICA), which assumes spatial invariance, is known in the art. That is, the assumption is made that mixing matrices of the sources represented in nearby pixels are the same. Spatial invariance assumptions are appropriate for images with high pixel on target values (that is, an image of a large tumor), but lead to significant error when applied to images with small pixel on target values (that is, an image of a small tumor or pre-tumor). Thus, harnessing the ICA algorithm to detect small growths or other such aberrations that can not characterize the early stages of a pathological disorder.

In addition, a Fast Simulated Annealing algorithm by H. Szu is known in the art (Szu and Hartley, "Fast Simulated Annealing", Physical Letters A, volume 122, number 3, pp. 157-162, 1987, the contents of which are incorporated herein by reference).

SUMMARY OF THE INVENTION

Overview of the Present Invention

A closed, warm room at a temperature T, if left alone, will become messy at a maximum entropy S by Shannon's Theorem. When energy (that is, input/output or I/O) is applied to the room, then the room will be less messy, reaching a most probable trade-off state. Likewise, there are multiple routes to travel to New York City from Washington, D.C., and, given a data vector [X], the most probable route to travel (that is, the source vector [S]) from Washington, D.C. to New York City would be the route which requires the least amount of energy and the least time, and would typically be taken as a common-sense way by thousands of travelers.

The present invention postulates that the information (I/O) energy E as a first order, feedforward estimation error energy, and adopts the isothermal equilibrium condition at the minimum of the Helmhotz free energy H=E−TS. This generalized information theory for open dynamic equilibrium becomes an aspect of the resolution of multiple choices of solutions as the unique solution. The present invention claims the application embodiments of this new theory.

One requires multiple sensors to measure multiple features to cover all possible sources with enough signal-to-noise ratio, then their unknown mixture may be de-mixed in the smallest possible image size, single pixel emitted from an unknown source medium, e.g. tissue and surrounding. This single-pixel nonlinear blind de-mixing algorithm (or procedure or method) of the present invention is unique because the present invention imposes the minimum Helmholtz free energy for the most probable equilibrium situation, and thus does not use the neighborhood pixel gray values in order to seek the mathematical transformation that leads to the factorization of the joint-probability-density function (which is the theory of Independent Component Analysis (ICA) which works only for there are enough number of pixels over a large size of tumor to form the probability distribution).

The present invention measures multiple radiation components forming a data vector per single pixel $X=(X_1, X_2)$ in order to determine uniquely the underlying sources forming a source vector $S=(S_1, S_2)$ propagating through a non-linear mixing medium. The present invention adopts that the thermal diffusion is constrained isothermally at the equilibrium free energy, known as Helmholtz free energy: H=E−T S where E is the energy, T is the equilibrium reservoir temperature and S denotes the classical Shannon information theory entropy. In this sense, present invention generalizes the classical Shannon information theory, which states the special case of a closed system E=0 and the entropy must be evolving toward the maximum for the absolute equilibrium. The present invention postulates the state of an open equilibrium system defined by the feed-forward first order error energy $E(X/S)=\mu\{g([W]X)-S\}$. The present invention seeks among all possible vector sources $S=(S_1, S_2)$ the one that satisfies the minimum H for arbitrary mixing matrix [A] and smooth nonlinearity g: $X=g^{-1}\{[A)]S\}$. This physical condition of isothermal equilibrium is a strong constraint which permits the present invention to invert the single-pixel data blindly for S, without knowing ahead the mixing matrix and non-linearity.

The present invention departs from the traditional ICA solution, which must use the additional neighborhood pixel data by furthermore assuming the space-invariant imaging condition, namely an identical [A] for all pixels so that using neighborhood data will not increase more unknowns. Unfortunately, this space-invariant condition is valid only when many pixels cover a very large tumor. In medical diagnosis, one wishes to detect early the smallest possible malign tumor, of which the heat transport mixing matrix [A(pixel)] must in general vary from its home pixel to its neighborhood.

The practice of this patent has demonstrated the possibility of an early detection by taking two pictures using two spectral cameras non-intrusively. Each pair of input pixel data vector has two components, a long wavelength (8-12 micrometer) and a middle wavelength (3-5 micrometer). Such a pair per pixel is defined as a vector X(pixel, t)= $(X_{long}(pixel, t), X_{short}(pixel, t))$, where t indicates a repetition time that can reveal the growth of a malign tumor which is usually mixed with a benign one in terms of a unknown percentage source vector S(pixel, t)=$(S_{benign}(Pixel, t), S_{malign}(pixel, t))$. This expectation is realistic because the physics of radiation source indicates a shift toward a shorter wavelength spectrum $X_{short}(pixel, t)$ associated with the massive nutrition feed of a warmer lymph and blood toward a rapid growth of a malign tumor (biologically known as the Angiogenesis property). Then, the quantitative value of the malign tumor source $S_{malign}/(S_{malign}+S_{benign})$ can be determined by imposing the generalized information theory at a local equilibrium in terms of the Helmholtz free energy.

Accordingly, an aspect of the present invention is an embodiment of a single pixel, non-linear blind de-mixing algorithm (or procedure) with pairs of nonlinear sensors that together can provide pixel by pixel nonlinear blind recovery of noisy heat source signals. The pixel by pixel blind recovery is thus possible for real time massively pixel-parallel implementation without latency associated with the batch mode signal processing. This feature is crucial for the real world space-time variant propagation medium.

The present invention provides an exact, global solution to the above-mentioned non-linear problem that is numerically based.

The single-pixel, non-linear blind de-mixing algorithm, or procedure, of the present invention is also referred to as a non-linear Lagrange Constraint Neural Network (non-linear LCNN, or unsupervised learning artificial neural network) algorithm, or procedure, and is an unsupervised algorithm (procedure).

A further aspect of the present invention is application of the single-pixel, non-linear blind de-mixing algorithm to general biomedical measurement and diagnoses systems. More specifically, neural network systems and devices embodying the single-pixel, non-linear blind de-mixing algorithm of the present invention are applied to the detection of cancers in the mammalian breast and blockages in the body fluid circulatory system by using single axis multiple-camera system.

Yet another aspect of the present invention is application of the single-pixel, non-linear blind de-mixing algorithm to the in situ multiple-mode fiberoptical data gathering or imaging devices.

A further aspect of the present invention is application of the single-pixel, non-linear blind de-mixing algorithm to the amplification hearing aids problem based on the two-ear binaural processing for de-noise echo cancellation and signal classification.

The algorithm, or procedure, of the present invention, referred to, variously, as single-pixel, non-linear blind de-mixing algorithm, a non-linear LCNN, and a feedforward Lagrange Constraint Neural Network (feedforward LCNN), makes pixel by pixel blind source separation (BSS) possible for real time implementation without latency associated with the batch mode signal processing based on stochastic ICA, and without the latency associated with supervised algorithms. This feature is important for the real world space-time variant propagation medium.

One assumption made is that the unknown sources are equally probable and seek optimization balanced by the constraints of data measurement model times the Lagrange Multipliers.

The present invention is directed to a single-pixel, non-linear blind de-mixing algorithm modeled on the human visual/brain unsupervised learning system and enables detection of heat radiated by abnormally reproducing breast cancer cells.

The single-pixel, non-linear blind de-mixing algorithm of the present invention, is based on the Lagrange Constraint Neural Network (LCNN) and multiple spectral data per pixel, and enhances the sensitivity and accuracy of breast cancer testing.

That is, the present invention includes methods and devices that passively detect changes in the body fluid flow by use of a sensor pairs smart processing system, including a digital heat spectrum local thermometer usable for core temperature maintenance, based on the single-pixel, non-linear blind de-mixing algorithm.

The sensor pairs smart processing system (including the single-pixel, non-linear blind de-mixing algorithm) is modeled on the human visual/brain unsupervised learning system and enables detection of heat radiated by abnormally reproducing breast cancer cells.

Abnormally reproducing cells demand greater nutrition through increased oxygen supply, thus generating higher concentrations of heat in specific areas. Applying the single-pixel, non-linear blind de-mixing algorithm of the present invention enables classification of the infrared heat distribution given off by these cells, and thus enables a digital heat spectrum local thermometer for core temperature maintenance.

The single-pixel, non-linear blind de-mixing algorithm per pixel of the present invention is based on the information derived directly from spectral data alone. To reveal the hidden spectral features included in a single pixel image data vector $X=[A]S$, the matrix must be inverted without knowing both the breast-medium heat-transfer matrix (MTF) $[A]$ and the heat source $S$ which both vary from pixel to pixel, and the single-pixel, non-linear blind de-mixing algorithm provides the solution to reveal these spectral features.

The single-pixel, non-linear blind de-mixing algorithm of the present invention is a space-variant imaging algorithm. The single-pixel, non-linear blind de-mixing algorithm of the present invention following spectral data vector analysis and the physics constraints of thermodynamics free energy minimization achieves subpixel accuracy.

With the single-pixel, non-linear blind de-mixing algorithm of the present invention, similar to a pair human eyes, a pair of cameras at different infrared wavelengths (Medium wavelength IR (3-5 micrometers) camera and Long wavelength IR (8-12 micrometers) camera, both having about 10 milli Kelvin degrees in the minimum resolvable temperature difference (MRTD)) transcribes this thermal diffusion process into two images, which are then filtered for shared signals while disagreement noise is minimized. This process detected early stage ductal carcinoma in situ (DCIS) in a test patient using a double-blind procedure.

The present invention provides multispectral, sub-pixel super-resolution potentially more accurate than current methods by an order of magnitude, and offers a passive, inexpensive, non-intrusive, convenient means of screening pre-cancer patients without radiation hazard, and may potentially detect in situ carcinomas long before a mammogram might detect them.

The application of the single-pixel, non-linear blind de-mixing algorithm of the present invention may offer an unbiased, more sensitive, accurate, and generally more effective way to track the development of breast cancer than the thermal breast scanning of the related art, without demanding the variables of along wait in a cold room, increasing the variability inaccuracy in thermal detection and causing patient discomfort.

The single-pixel, non-linear blind de-mixing algorithm, which is an unsupervised classification algorithm, of the present invention applied to multispectral imagining potentially improves the early detection process for breast cancer and possibly other dermal carcinomas.

The present invention emphasizes a single-pixel, non-linear blind de-mixing algorithm without using statistics. In single-pixel, unsupervised learning of the present invention, one's own library is built. Moreover, unsupervised algorithms do not face the hindrances of supervised algorithms discussed herein above related to building and maintaining libraries.

Moreover, the present invention includes blind signal separation of detailed algorithms specific to the function of neural networks.

The present invention assumes spatial variance to address the problem of unknown mixture characteristics and original sources. Thus, the present invention has the capability to find sub-pixel irregularities such as tumors and track their behavior over time. Such abilities lead to greater insights in medical inquiries relating to how and why such abnormalities originate and burgeon.

Moreover, the present invention relates to the method and devices for passively detecting changes in the increase or decrease of thermal flow by the use of the single-pixel, non-linear blind de-mixing algorithm based on the Statistical Mechanical thermodynamics principle of unsupervised fusion of sensor pairs. More specifically the embodiment of unsupervised fusion of sensor pairs, known as artificial neural networks, is applied to general biomedical instrument measurement and diagnoses systems. Most specifically the neural network system (which is coined as Lagrange Constraint Neural Network—LCNN, or feedforward LCNN) and a device are applied to detection of cancer in the mammalian breast and hot spots of rheumatic arthritis or conversely the blockages in the blood circulatory system that might be of importance for coronary artery bypass surgery, diabetes and deep vein thrombosis.

The system of the present invention, which includes the single-pixel, non-linear blind de-mixing algorithm and supporting detection equipment is used to detect anomalies in the image. Additional biomedical applications of the single-pixel, non-linear blind de-mixing algorithm of the present invention include in situ data gathering or imaging using multiple mode fiberoptical sensing as well as selective amplification hearing aids through two-ear binaural processing for de-noise echo cancellation and signal classification.

The single-pixel, non-linear blind de-mixing algorithm of the present invention is referred to, variously, as the feedforward LCNN, the sensor pairs smart processing system, unsupervised smart (learning) algorithm, general brain like smart algorithm, feedforward LCNN unsupervised learning algorithm, non-linear LCNN, and unsupervised nonlinear feedforward Lagrange Constraint Neural Network (LCNN) signal and image classification procedure.

These together with other aspects and advantages which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIGS. 10A and 10B illustrate solution of the 4D optimization problem by means of the exhaustive search technique that yields global minima of the error energy function (15) as a solution for the unknown nonlinearity slope parameter α and magnitude of the source vector N 1002 as well as two killing angles perpendicular to the unknown mixing angles 1004.

The single pixel, non-linear blind de-mixing algorithm (or procedure) of the present invention is embodied in hardware, software (as a computer program), or a combination of both, as discussed with respect to the following FIGS. 17-30A and 30B.

Figure 17:
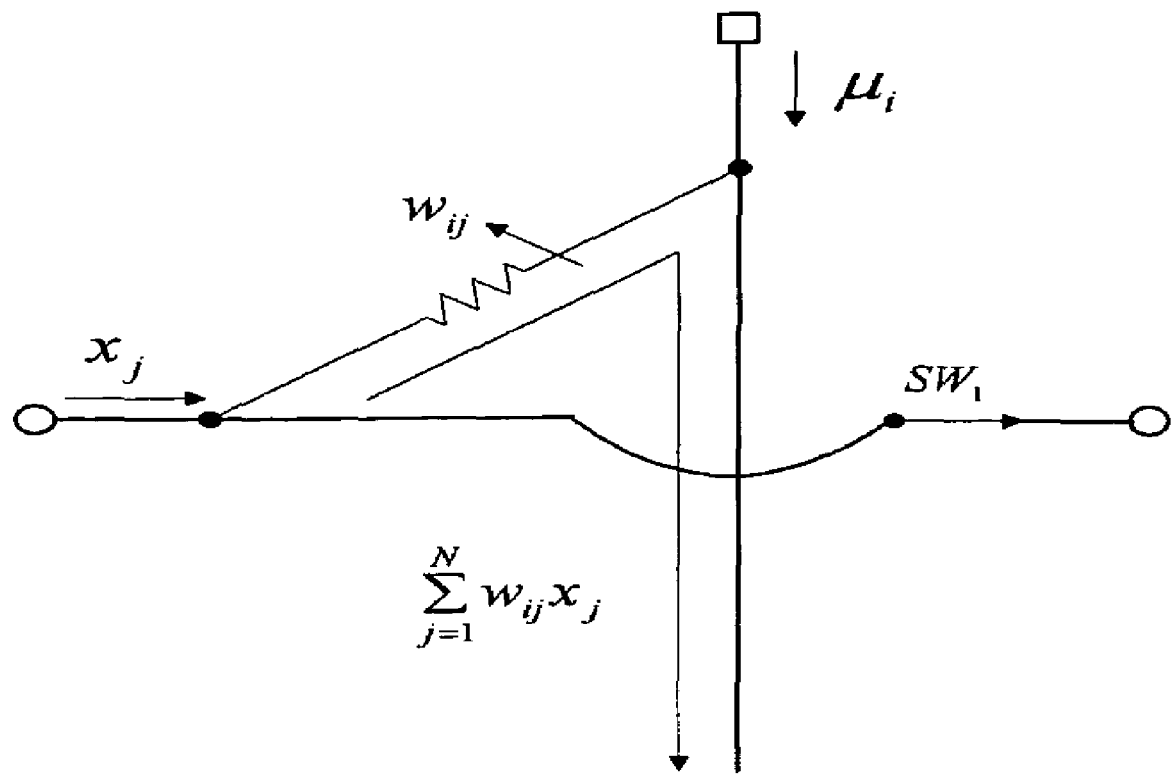

FIG. 17 is a present invention related single unit circuit diagram of the feedforward LCNN method (the single pixel, non-linear blind de-mixing method of the present invention).

FIG. 18 shows a description of computational processes of the present invention for the single unit circuit diagram shown in FIG. 17, of the linear feedforward LCNN method (the single pixel, non-linear blind de-mixing method of the present invention).

Figure 19:
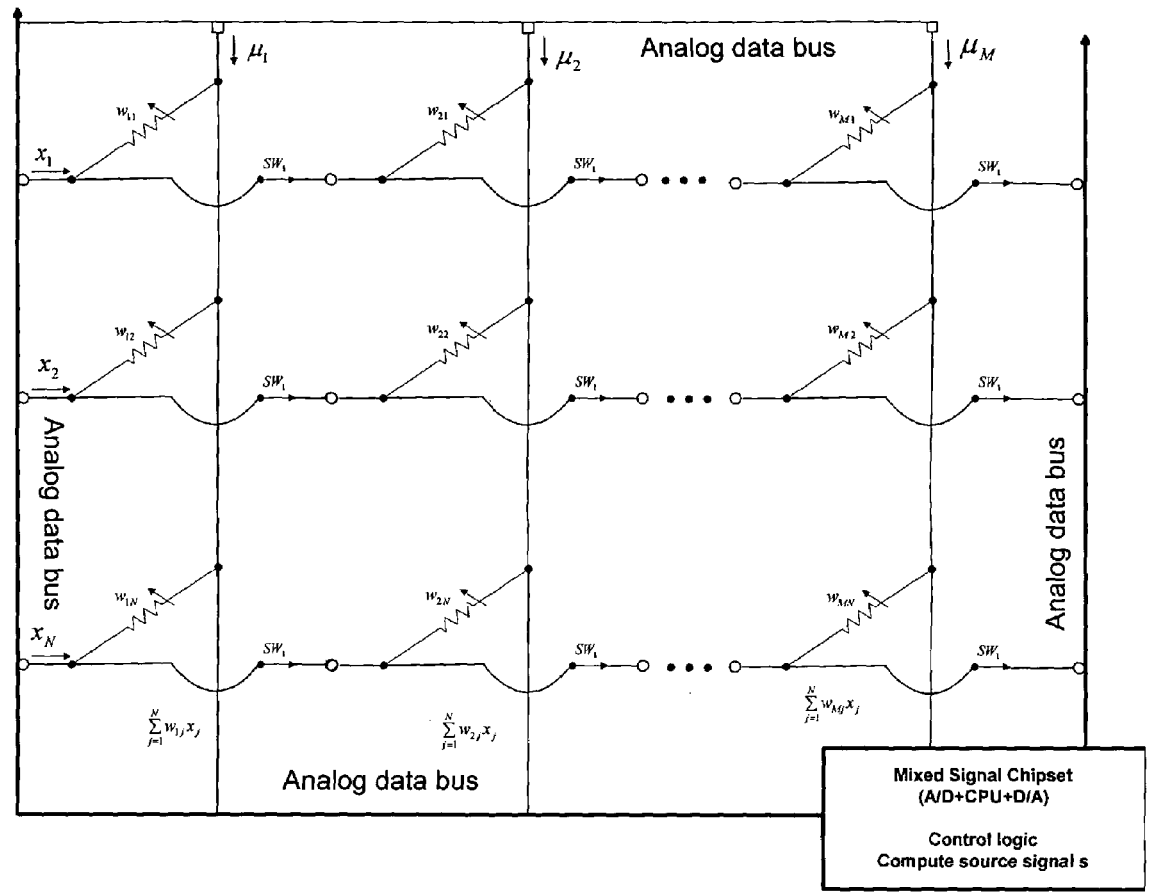

FIG. 19 shows the present invention related feedforward LCNN (single pixel, non-linear blind de-mixing of the present invention) circuit diagram.

Figure 20:
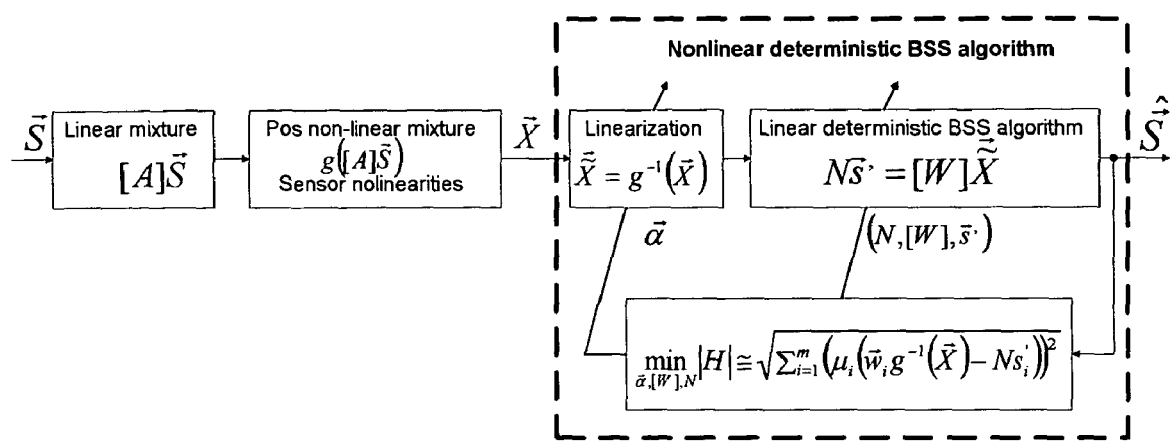

FIG. 20 is a present invention related illustration of the two-stage nonlinear LCNN algorithm (the single pixel, non-linear blind de-mixing algorithm of the present invention) that includes linearization and de-mixing stages 2004.

Figure 21:
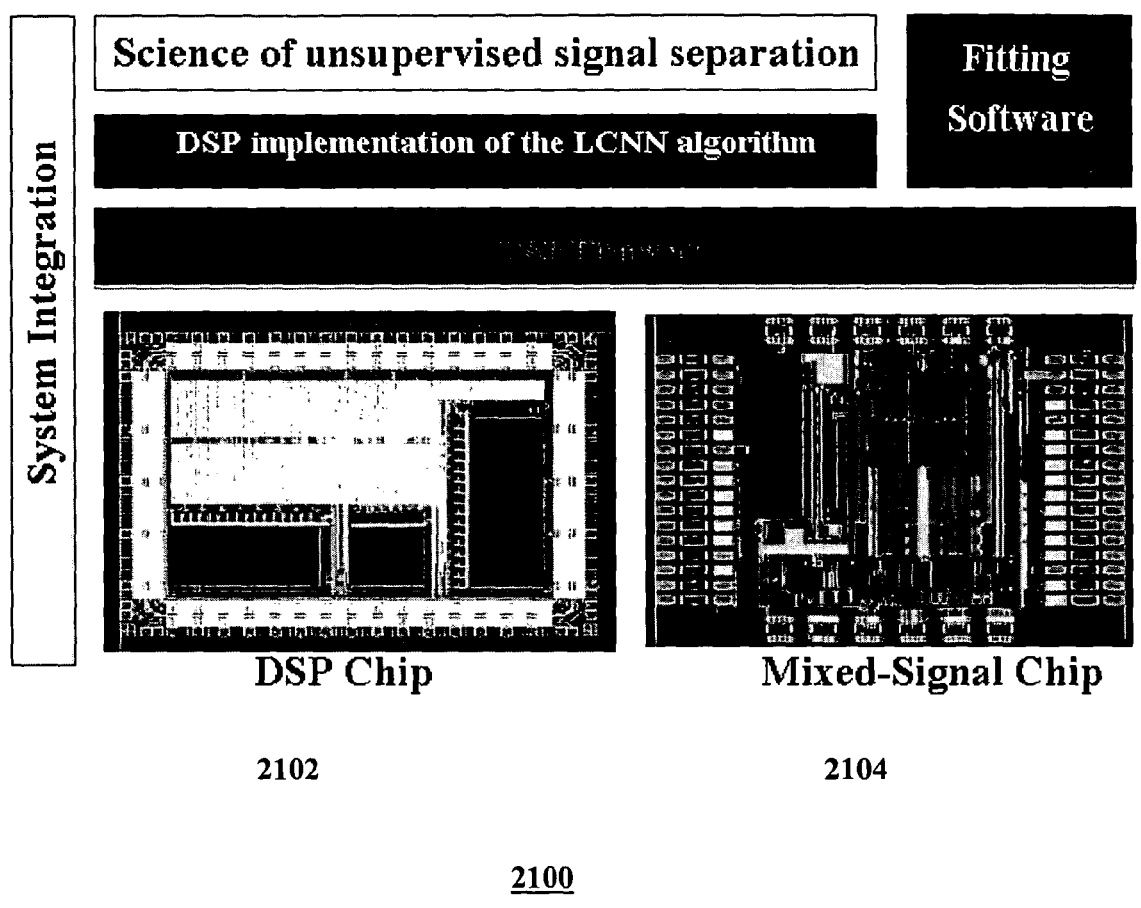

FIG. 21 illustrates how the feedforward LCNN (the single pixel, non-linear blind de-mixing algorithm of the present invention) shown on FIGS. 16-19 represents a scalable solution for a 0.25 μm VLSI implementation.

Figure 22:
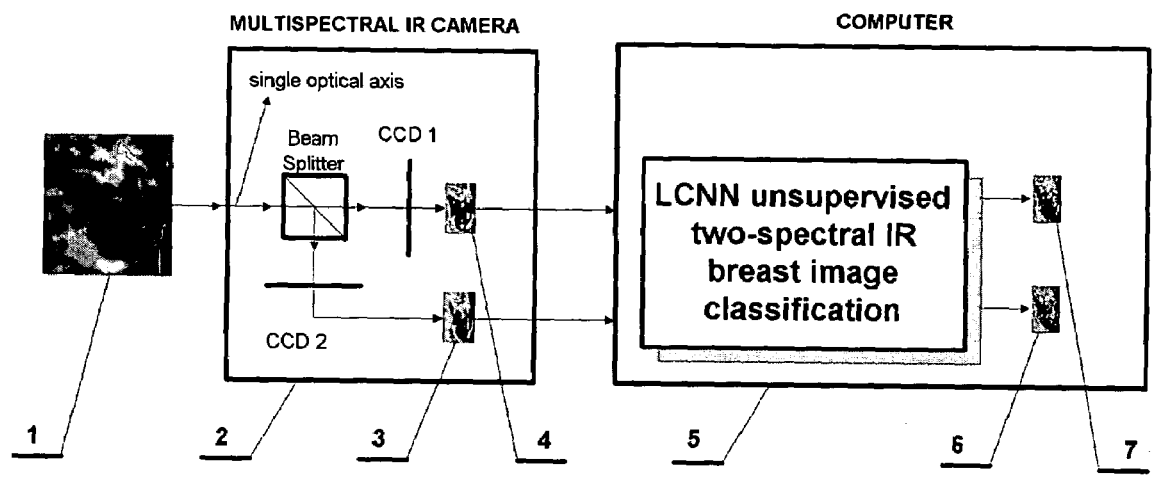

FIG. 22 shows the present related two-spectral single optical axis breast imaging system which enables more accurate pre-cancer ductal carcinoma in situ (DCIS) tumor classification and diagnosis than standard single color breast imaging or X-ray based mammography. Data model X=[A] S, Eq.(3), is related to FIG. 22 as follows. Two images after beam spliter are part of the data vector X 2202. Two images at the output of the LCNN algorithm 2204 are source images S. Eventually one of the source images corresponds with the tumor.

Figure 23:
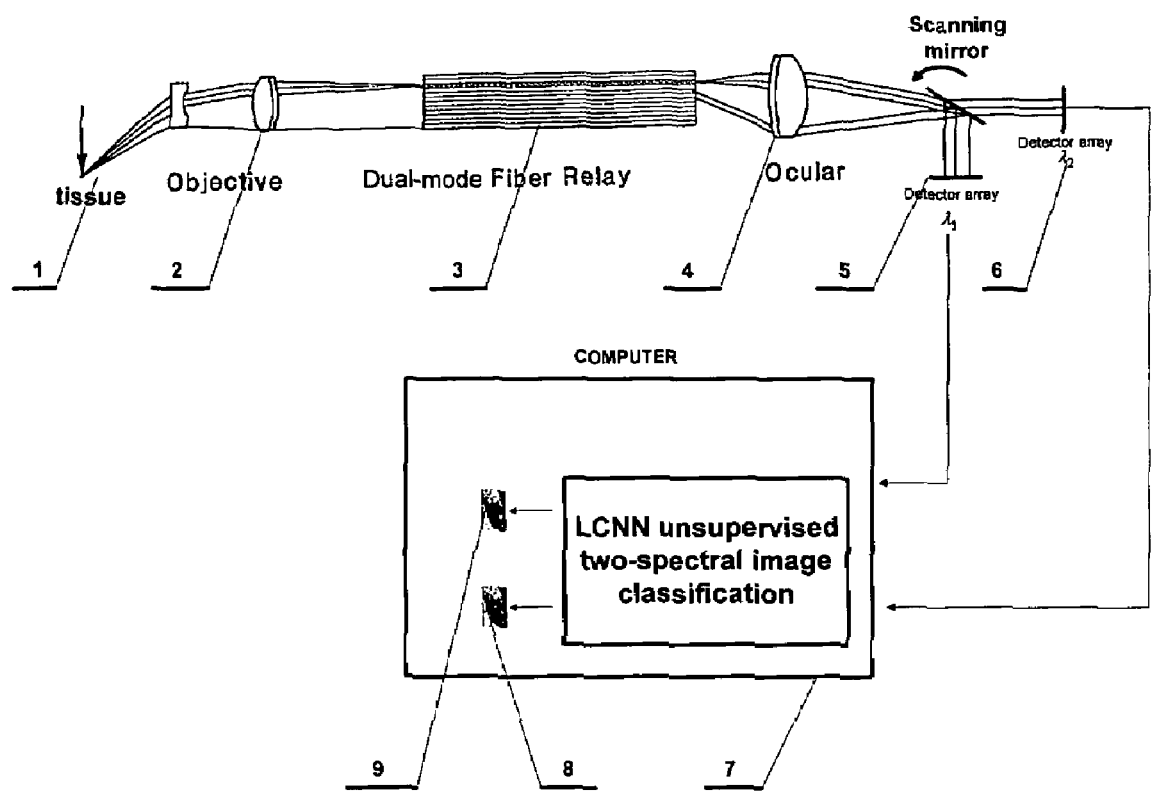

FIG. 23 shows an optical layout of a dual-mode fiberoptic endoscope system of the present invention. Data images X are outputs of the detector arrays 2302 and source images S are at the outputs of the LCNN algorithm 2304.

Figure 24:
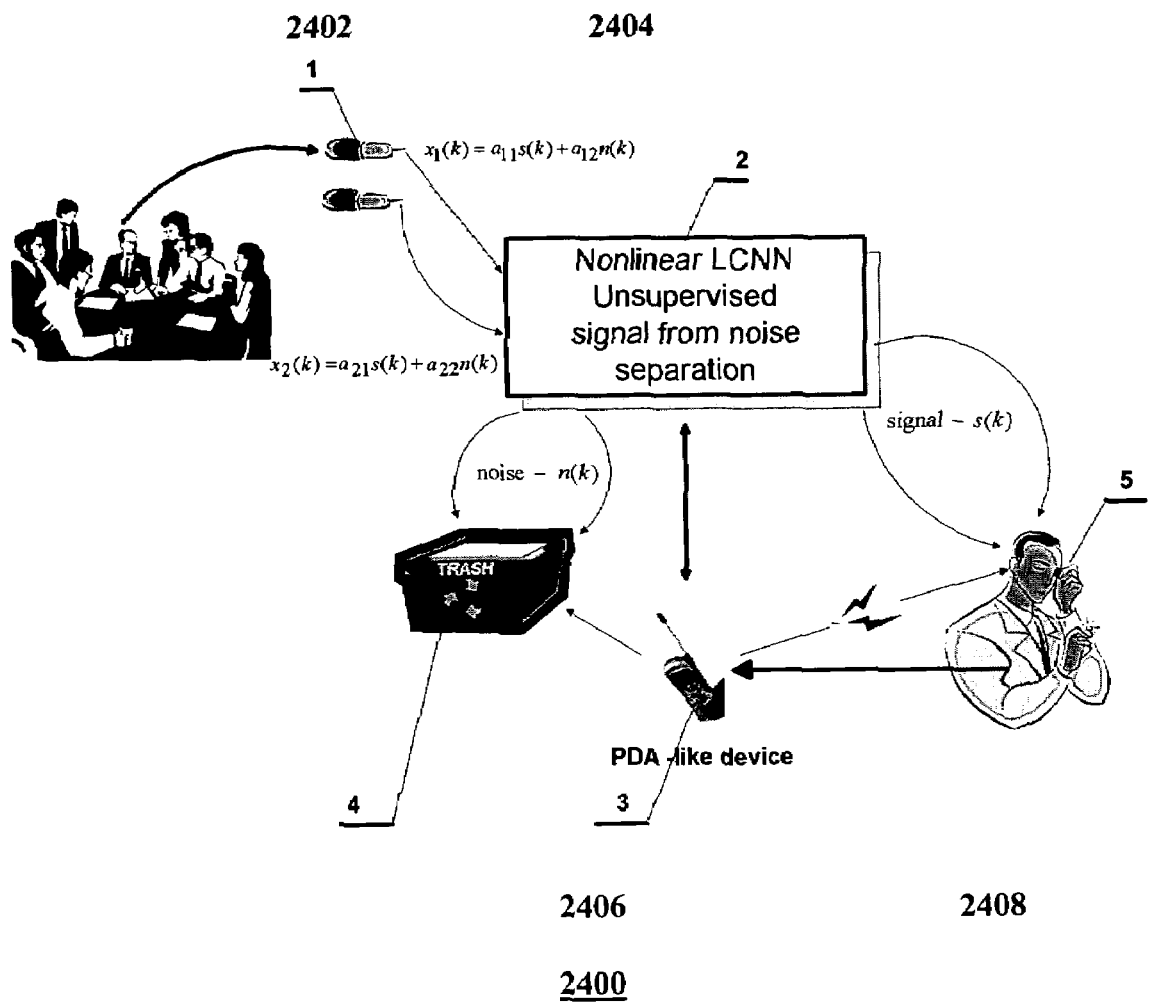

FIG. 24 shows a selective amplification hearing aids system by means of two ears-like binaural nonlinear feedforward LCNN signal processing (the single pixel, non-linear blind de-mixing procedure of the present invention). Data vector X is related to the sensor outputs 2402 while source vector S is related to outputs of the LCNN algorithm with one component as a noise 2406 and another one as a signal 2408.

Figure 25:

FIG. 25 shows a long IR (8-12 μm) image of the breasts which represents first component of the data vector X.

Figure 26:

FIG. 26 shows a mid IR (3-5 μm) image of the breasts which represents second component of the data vector X.

Figure 27A:
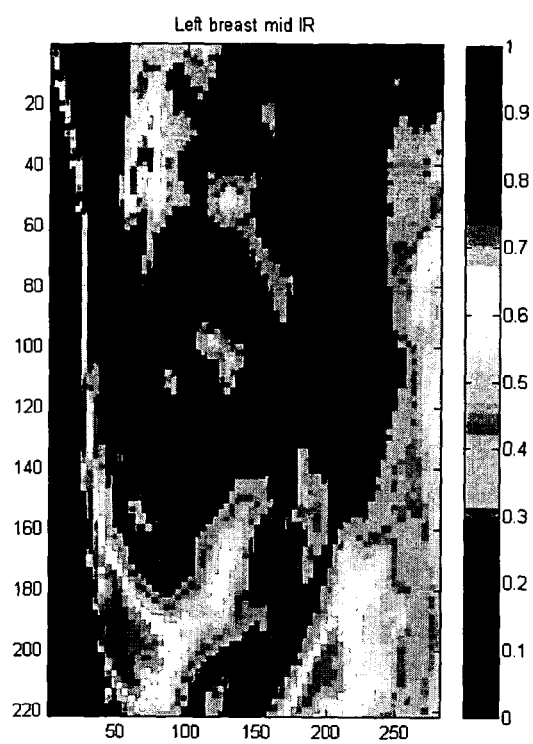
Figure 27B:
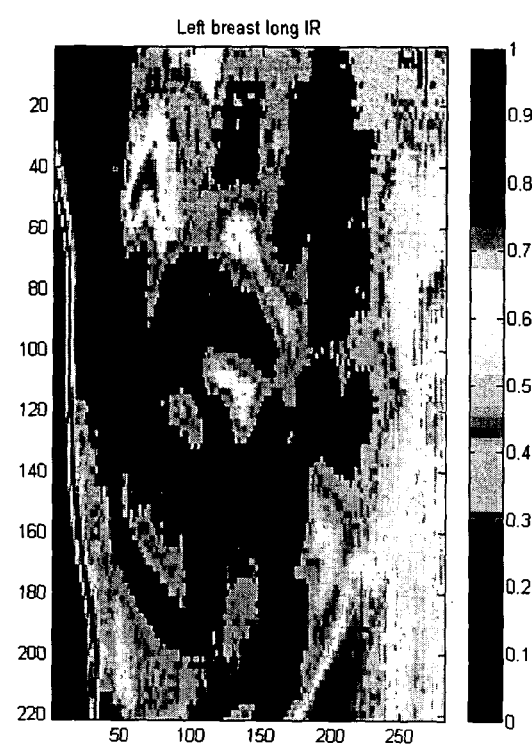

FIGS. 27A and 27B show the registered mid IR and long IR images, respectively, of the right breast. First component of the data vector X is given with 2702 and second component of the data vector X is given with 2704.

Figure 28A:
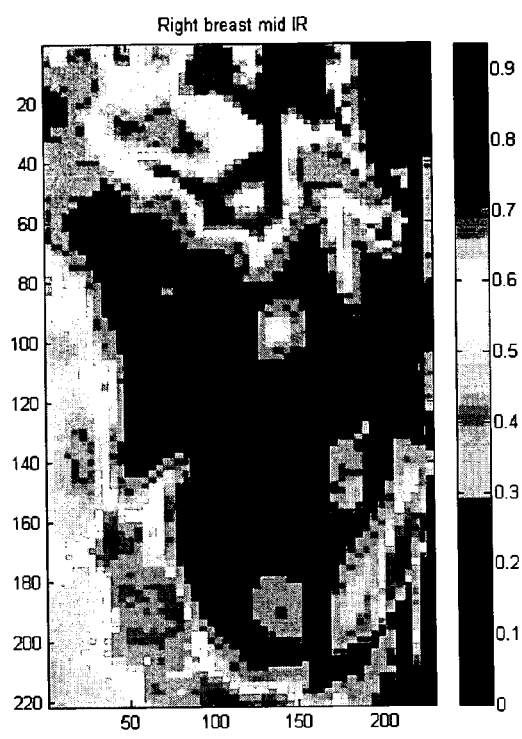
Figure 28B:
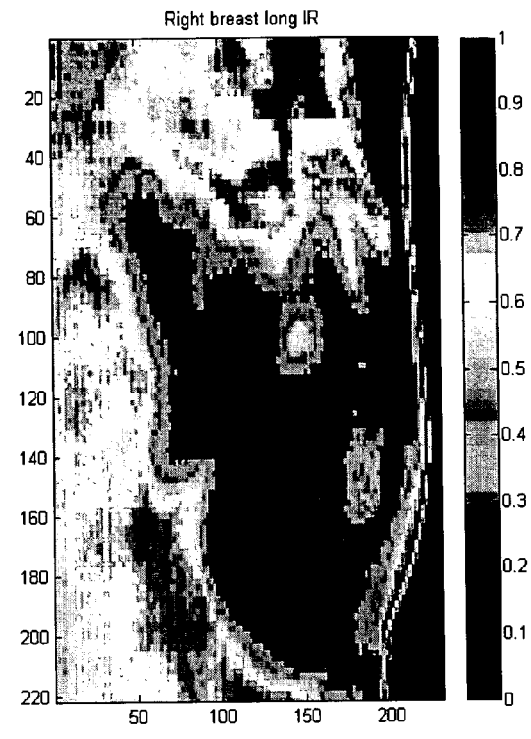

FIGS. 28A and 28B show the registered mid IR and long IR images, respectively, of the left breast. First component of the data vector X is given with 2802 and second component of the data vector X is given with 2804.

Figure 29A:
Figure 29B:

FIGS. 29A and 29B show the LCNN de-mixed images of the right breast, de-mixed using the single pixel, non-linear de-mixing procedure of the present invention. First component of the source vector S is given with 2902 and second component of the source vector S is given with 2904.

FIGS. 30A and 30B show the LCNN de-mixed images 3002, 3004 of the left breast, de-mixed using the single pixel, non-linear de-mixing procedure of the present invention. First component of the source vector S is given with 3002 and second component of the source vector S is given with 3004.

DETAILED DESCRIPTION OF THE PREFERRED EMBODIMENTS

Overview of the Present Invention

An overview of the present invention is now presented in terms of a number-theoretical description of the philosophy of the present invention.

Without presenting the analytical solutions, the single-pixel, non-linear blind de-mixing algorithm of the present invention may be intuitively justified as follows. Human beings are endowed with two pairs of sensors. Two ears, two eyes, one nose but two passages, one tongue but two sides and front-back, two hands, two feet, groups of tactile sensors that generate the vector but not scalar time series, may be taken for granted. The vector data allows searching of the subspace where the unknown mixing vectors span by the concept of a killing or elimination weight vector. One possibility for having two sensors is if one is damaged, the other would still be available. That certainly gave a hardware fault tolerance, so-to-speak.

Figure 5:
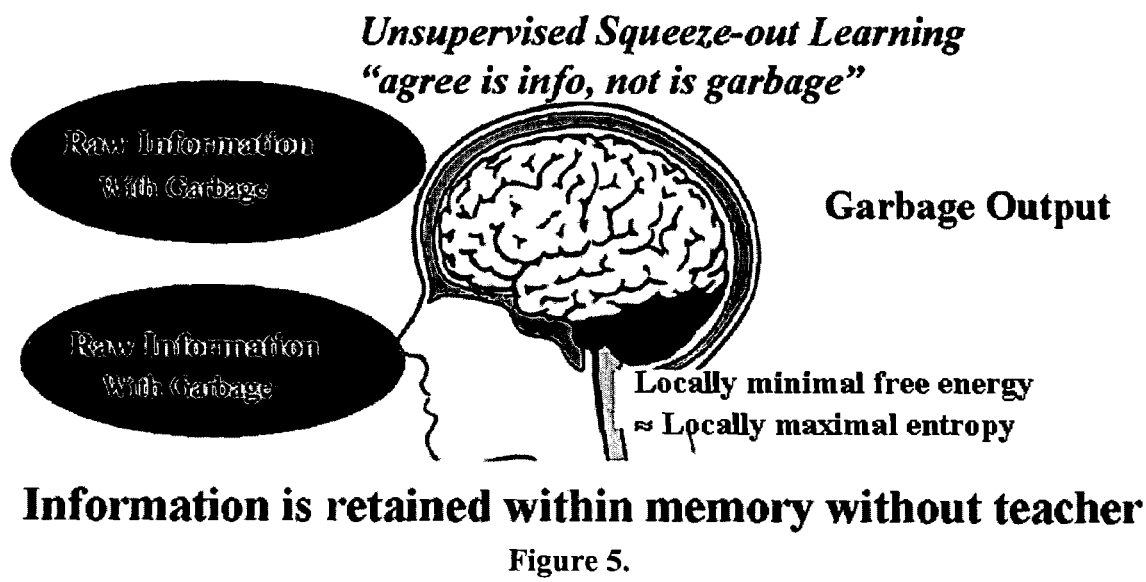
FIG. 5 is an illustration of the present invention related to a general brain-like unsupervised fusion of sensor pairs 500 (the single pixel, non-linear blind de-mixing algorithm of the present invention) where information is extracted from the data input and retained within a memory through a locally minimized free energy what implies locally maximal entropy.

In addition, being more sophisticated and learning, like a bat, two sensors together could provide direction finding. Indeed, human beings are equipped with a true-time delay filter bank having about a milli-second acoustic propagation time difference across two ears. More importantly, these sensors are used for a learning strategy without the need of a teacher and its guidance delay: "while two sensors disagreed it should be noise, agreement should be signal", FIG. 5. More particularly, FIG. 5 is an illustration of the present invention related to a general brain-like unsupervised fusion of sensor pairs (the single pixel, non-linear blind de-mixing algorithm of the present invention) which is based on the minimum Helmholtz energy squeeze learning strategy "raw pairs of data in and garbage out" that requires no teacher.

For example, if someone called out your name in a windy hill for an imminent danger, your two ear could immediately reject the wind noise by comparison and selectively amplified the agreed signal for a quick response in turning ones head for an immediately second hearing and looking. With the help of the short term memory, one has four ears and four eyes, from which the degree of agreement could be ranked in order that allowed the coincidence amplification to sharpen the sighting and hearing. These provide intuitive reasons why the present invention includes a pair of microphones to eliminate the recording wind noise, similarly binaural hearing aids, as well as two infrared cameras at distinct different infrared spectral bands in order to image the angiogenesis process and process the data fusion in a brain-style smart processing.

How could the brain achieve biologically the smart sensor processing without a teacher? When the external signals entered through a set of sensors into the brain, hundred millions excitations were generated by sensory neurons that took a lot of energy to sustain and therefore most of all redundancy would have to be decaying toward random brain waves to make room for further stimulus. What happened along the way of the naturally decaying process. Did the neuron-pathway take the advantage of the inevitable decaying to learn something? This suggests that the energy decaying process is naturally driven by the second law of thermodynamic that says that "as the energy diffuses, the entropy always increases". The entropy increase processing needed no teacher because, for whatever the inputs the outputs at, the finish of learning happened at an energy minimization and local maximum entropy characterization of randomized diffusion of brain waves. Such an unsupervised learning of ANN had successfully reproduced the minimum redundancy correlation set of sensor pairs inputs in the form of oriented edge maps observed in cats first by Hubel and Wiesel in the multiple octave resolution. In the lowest resolution of pair sensor agreement, one's represented the binary agreement and the disagreement by zeros, and the location of the sparse one's is different from other oriented edges in the two-dimensional (2D) space. In so doing, the synaptic weight matrix among neurons extracts the edge features without the need of a teacher since the identical de-correlated outputs required no teacher to specify it for any inputs. A person with one eye could learn without a teacher by trying harder width the help of hardware multiplexing using internal memory by taking a second look. Such a capability of unsupervised learning turned out to be the key-learning ingredient of advanced Machine-IQ beyond the average robots.

Figure 6:
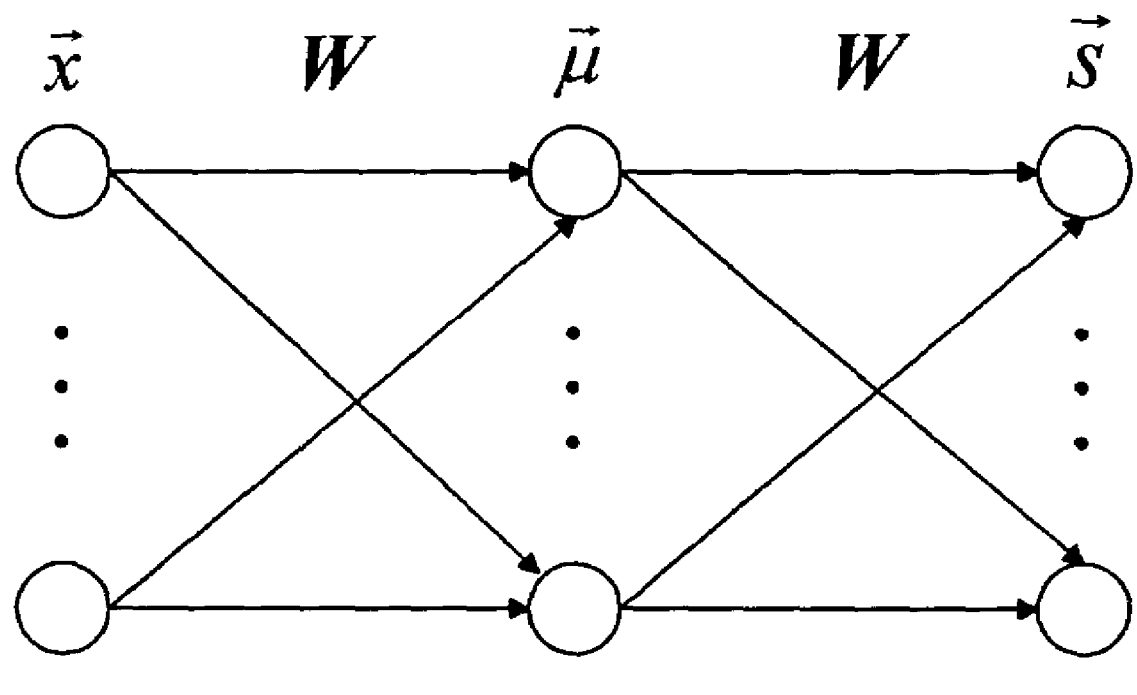
FIG. 6 is the single pixel, non-linear blind de-multiplexing algorithm 600 (the feedforward LCNN MaxEnt Neural Network) of the present invention which is using the source ensemble average for the stochastic gradient that might have different mixing matrix [A] for each pixel and enjoyed the real-time pixel-by-pixel computation.

Real world applications are mostly nonlinear or pseudo-linear. The present invention addresses the real world applications that are either nonlinear or linear by means of the second law of thermodynamics formulated in terms of the Lagrange Constraint Neural Network (LCNN). The linear LCNN algorithm is a special case of the nonlinear LCNN version (the single pixel, non-linear blind de-mixing algorithm of the present invention). A feedforward version of the LCNN (the single pixel, non-liner blind de-mixing algorithm of the present invention) 600 is shown in FIG. 6. FIG. 6 is the single pixel, non-liner blind de-multiplexing algorithm 600 (the feedforward LCNN Neural Network) of the present invention which is using the source ensemble average of the stochastic gradient that might have different mixing matrix [A] for each pixel and enjoyed the real-time pixel-by-pixel computation. Here, the feedforward term means that learning is formulated in terms of the [W] matrix that represents the inverse of the mixing matrix [A].

The single pixel, non-linear blind de-mixing algorithm of the present invention is formulated on a pixel by pixel basis and consequently does not suffer from blurring effects due to pixel ensemble averaging operations.

In multispectral imaging applications (remote sensing, breast cancer detection, fiberoptic data gathering in tissue) the pixel ensemble average property will cause a loss of details that in some cases (breast cancer detection, detection of small objects in the remote sensing) could be unacceptable. The single pixel, non-linear blind de-mixing algorithm used the source ensemble average for the stochastic gradient that might have different mixing matrix [A] for each pixel and enjoyed real-time pixel-by-pixel computation.

The acceptance of a new procedure, single pixel, non-linear blind de-mixing procedure, depended on its ability to make predictions. The thermodynamics entropy balance existed naturally in LCNN between the action and the reaction. On the other hand, there were those emotional Intelligence Quotient (e-IQ) that is known to like action and reaction influence our thought processes, "thinking through feeling", which were emotion, timing, rhythm, guts feeling, body temperature etc. How could such novel capability be substantiated with the ANN model? The single pixel, non-linear blind de-mixing algorithm accomplishes that because the single pixel, non-linear blind de-mixing algorithm predicted something else other than the neurons themselves must be involved in unsupervised learning. Without the external detail supervision, Lagrange constraints from the environmental heat reservoir $\vec{\mu}$ 600 provided the necessary reaction forces to balance the action of neuron excitations generated by input data $\vec{x}$ 600. The brain anatomy revealed that there were neurons firing rate binding modulating the synaptic weights for information processing and memory. In addition to neurons in the brain, millions of housekeeping cells whose active role in information processing was suspected but not yet been verified.

Theory of the present invention seemed to suggest that the Lagrange constraint forces play the role of those millions of cells doing more than the housekeeping of neurons activity but also maintaining the dynamic equilibrium of thermal reservoir. Thus, both neurons' actions and housekeeping cells reactions were simultaneously present in the single pixel, non-linear blind de-mixing algorithm, which is an LCNN model of ANN.

Since the sensor data vector $\vec{x}$ has the physical dimensionality of Volts, about 100 milli-volts across the axon synaptic junction as measured by 1952 Nobel Laureate Hodgkin and Huxley, the Lagrange constraints $\vec{\mu}$ that multiplied the data $\vec{x}$ to produced the internal energy U must have the physical dimensionality of Amperes, pico-Ampere per ion channel measured by 1991 Nobel Laureates Neher and Sakmann in the dendrite tree as an active data pre-processing. It represented the housekeeping tutor for unsupervised learning truly without an outside teacher. Any direct or indirect evidences in biological and neuropsychological experiments of homeostasis unsupervised learning theory would be timely. The hypothalamus that sits above the pituitary gland, so-called "third eye" in animal kingdom, located right at the geometric center of the brain, and can regulate many functions of brain and body. For example, the body temperature for a warm blood homeostasis animal is kept at a fixed temperature (37° C. for most human) in order to maintain a proper activity of the immune system and the enzymes catalytic reaction rate that balances the chemical reaction by a negative feedback system by means of the hormonal pathway (organic molecules e.g. antidiuretic hormone (ADH) regulated through the membranes, the intracellular (thyroxin to mitochondria), and the blood stream (e.g. adrenal, an enlarged ganglion, secrete adrenalin versus Amygdale fear and the depression Serotonin versus neurotransmitter). The balance is further controlled by the limbic (loop circuit) system connecting the Cerebral Cortex with the hypothalamus and the pituitary gland to translate complex emotion and drive into actions that in turn guide the motion perception and learning experience. From the definition of thermodynamic Helmholtz free energy, a constant cybernetic temperature To allows simultaneously minimizing the internal energy for supervised categorization and the maximization of the entropy for unsupervised component analysis.

Mathematically, artificial neural network models of unsupervised learning seemed to predict a constant temperature To for minimization of the thermodynamic Helmholtz free energy, $H=E-T_0 S$. While the supervised learning (with implicit or explicit teaching) may be driven by the internal energy minimization, the unsupervised learning (sensory pre-processing) may be driven by the relaxation decaying processes by means of the maximization of local entropy. These models suggest it may also be important to the intercellular communication-mediated learning mechanism. Furthermore, minimization of the Helmholtz free energy $H=E-T_0 S$ at a constant $T_0$ that involves the internal energy E and the entropy S is believed to have maintained the thermodynamic equilibrium of those intercellular communication mechanisms useful for Hebbian synaptic modification.

Infrared (IR) breast imaging using the single pixel, non-linear blind de-mixing procedure of the present invention is based on all long, mid, and short infra-red (IR) wavelengths simultaneously capable for fusion and classification as the present invention is accomplished 2202 based on the human brain pairs sensor unsupervised learning. Two color IR images registered properly 2204 could provide physicians with better breast cancer diagnosis. Two registered color images 2204 are components of the data vector X and represent inputs to the LCNN algorithms. Outputs of the LCNN algorithms 2204 are components of the source vector S. Unlike mammography which includes radiation hazards, there is no such risk in the passive two-color IR screening 2200. In a case of massive deployment of U.S. Department of Defense (DoD) IR technology for the first-line home defense that will imply low cost of IR technology based medical equipment.

In situ fiberoptical data gathering or imaging devices using the single pixel, non-linear de-mixing procedure of the present invention 2304 would be based on multiple mode fiber optical 2302 for multiple sensing 2300. Outputs of the multiple mode fiber 2302 are components of the data vector X while outputs of the LCNN algorithm 2304 are components of the source vector S.

Selective amplification hearing aids using the single pixel, non-linear de-mixing procedure of the present invention 2404 would take the advantage of two-ear binaural processing 2402 for de-noise echo cancellation and signal classification simultaneously. In two-ear binaural processing extracted signal is transmitted by a PDA-like device 2406 to an earpiece 2408. Components of the data vector X correspond with input to the LCNN algorithm 2404. Components of the source vector S correspond with the output of the LCNN algorithm 2404.

To differentiate benign from abnormal heat sources of the breasts by using the single pixel, non-linear blind de-mixing procedure of the present invention, a pair of infrared imaging cameras is used to be complimentary to the X-ray mammogram as a convenient, inexpensive and non-intrusive first-line defense, which could be recommended as a massive screening supplement as well as tracking the risky patients longitudinally in time as frequently as deemed to be necessary without the radiation hazard.

A contribution of the present invention is the single pixel, non-linear blind de-mixing procedure of the present invention together with the necessity of two cameras to take breasts' images simultaneously at two different spectrum bands (e.g. at the wavelength 1-3 μm or 3-5 μm & 8-12 μm) which is similar to the success of remote sensing at the satellite platform without the ground truth—"from tanks to tumors."

Indeed, U.S. Department of Defense (DoD) technology transition of Automatic Target Recognition (ATR) was traditionally implemented with a library of templates to determine close match with input data within a threshold. Unfortunately such a library approach could not be reliably applied to the breast thermal imaging that might vary according to capillary fluid flow constriction or dilation pattern that might be Angiogenesis carcinoma modulated by breast size, fatty tissue and skin textures to a lesser but unpredictable way.

The present invention includes an unsupervised classifier using the statistical mechanics based Lagrangian techniques in terms of the second law of thermodynamics contrast function, without relying on either the classical library hard templates or the modern artificial neural network (ANN) soft look-up extrapolation table based on supervised learning exemplars. Instead, following the biomimetics of two eyes, the present invention applies at least two imaging cameras FIG. 22 that give two spectral components of each pixel 2202 forming a vector data set $\vec{x}$. System designed such that data vector X already correspond with the source signal S is only a special case of the present invention.

Figure 7:
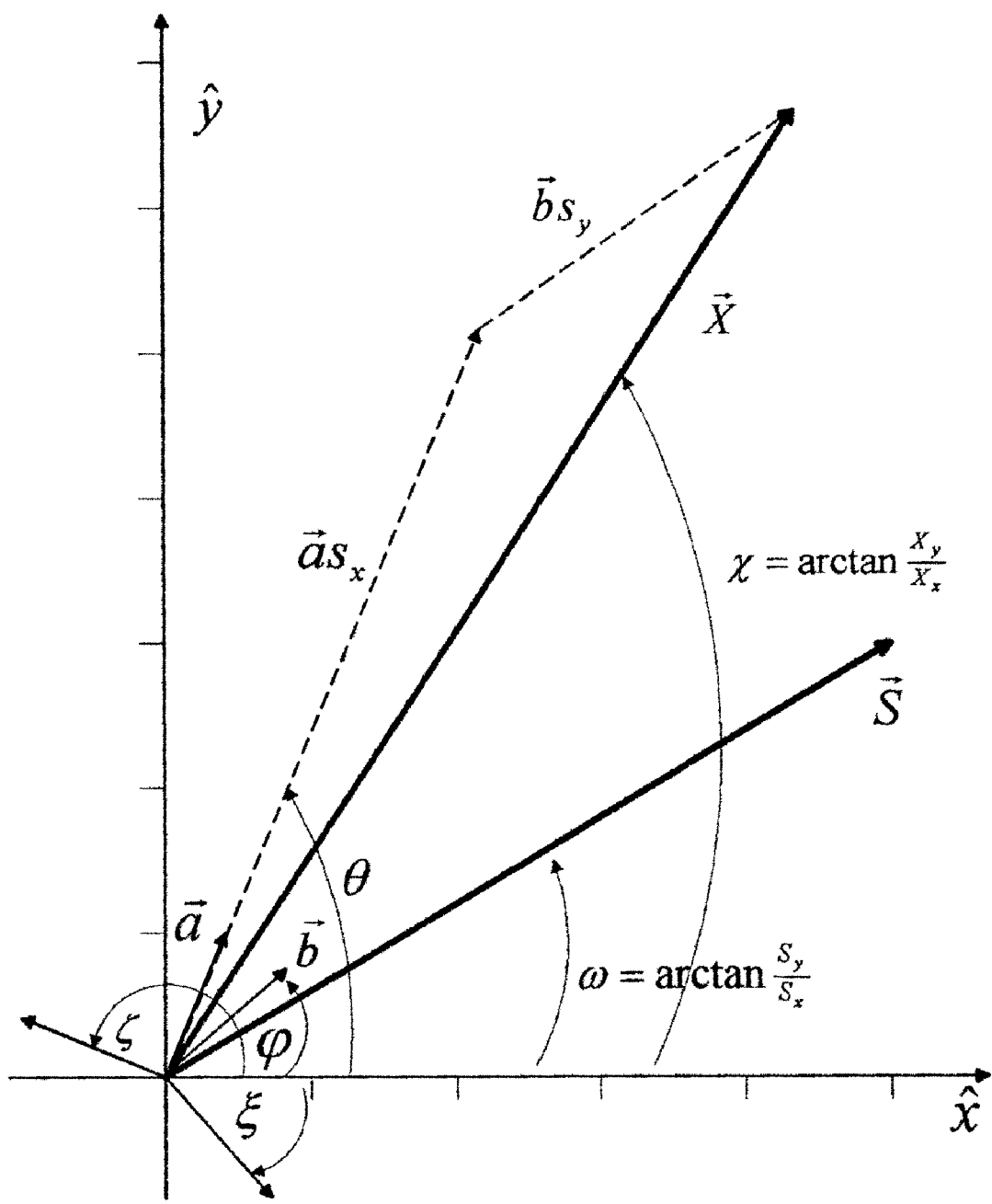
FIG. 7 is a Vector Space representation 700 of the killing vector approach to unsupervised learning where unknown feature vectors $\vec{a}$ and $\vec{b}$ (columns of the mixing matrix) are represented by the mixing angles and given data vector $\vec{X}$ always sits between them.

The present invention furthermore assumes that the breast tissue is a conservative propagation medium in the sense of neither sinks nor sources that the mixing matrix having two unit vectors that could be of any angles except in parallel FIG. 7. The reason why a pair could learn without a teacher might be explained by a unique orthogonal property that existed only in the vector domain called the vector inner product: given a mixture unit vector $\hat{a}=(a_x,a_y)^T$, one could exhaustively find in a subspace a unit weight vector $\hat{w}=(\hat{w}_x, \hat{w}_y)^T$ called the killing vector such that the summation of its products of the corresponding Cartesian components of the mixture vector happened to become zero.

$$(\hat{w},\hat{a}) \equiv \hat{w}^T \hat{a} = \hat{w}_x \hat{a}_x + \hat{w}_y \hat{a}_y = -\hat{a}_y \hat{a}_x + \hat{a}_x \hat{a}_y = 0 \quad (1)$$

According to the second law of thermodynamics, a suitable contrast function is the Helmholtz free energy so that one could systematically search the local minima generated by means of the killing weight vectors happened to nullify any one of two unknown mixing vectors. The mathematics is equivalent to a numerical game that might be called "name that numbers", similar to a popular TV show of "NAME THAT TONE". One had to guess what two positive integers in another person's mind were when that person gave two different combinations of these two hidden integers. The under-determined problem of special case of positive inverse problem is that 4 unknowns $(\theta,\phi,s_x,s_y)$ must be determined from two data $(X_x,X_y)$. In other words, each pixel of two images obtained from two cameras is considered as forming 2-D vector. Given the vector data per pixel to be two different combinations of pair integers say $s_x=5$ and $s_y=3$:

$$X_x = 5\cos\theta + 3\cos\varphi = 5x\frac{1}{\sqrt{5}} + 3x\frac{1}{\sqrt{2}}$$

$$X_y = 5\sin\theta + 3\sin\varphi = 5x\frac{2}{\sqrt{5}} + 3x\frac{1}{\sqrt{2}}$$

in unit of hundreds of photons in matrix form $$\begin{pmatrix} X_x \\ X_y \end{pmatrix} \equiv 8 \begin{bmatrix} \cos\theta & \cos\varphi \\ \sin\theta & \sin\varphi \end{bmatrix} \begin{pmatrix} 5/8 \\ 3/8 \end{pmatrix} \quad (2)$$

the question is what the unknown underlying sources 5 and 3 for the benign and abnormal heat sources were respectively. The corresponding vector version was:

$$\vec{X} = [\hat{A}]\vec{S} = s_x \hat{a} + s_y \hat{b} \quad (3)$$

$$= N(s'_x \hat{a} + s'_y \hat{b}) \equiv N[\hat{A}]\vec{S}$$

where $(\hat{x},\hat{a}) \equiv \cos\theta; (\hat{y},\hat{a}) \equiv \sin\theta; (\hat{x},\hat{b}) \equiv \cos\phi; (\hat{y},\hat{b}) \equiv \sin\phi$; The unit vectors were indicated by a hat. The corresponding vector diagram representation of the equations (2)/(3) is shown in FIG. 7. FIG. 7 is a Vector Space representation 700 of the killing vector approach to unsupervised learning. The data vector x̂ always sits between the unknown feature vectors â and b̂.

The unknown magnitude of the source vector per pixel N=5+3 is determined from the triangle inequality which applies for the vector norm as:

$$\|\vec{X}\|_2 \leq Ns'_x \|\vec{a}\|_2 + Ns'_y \|\vec{b}\|_2 = N(s'_x + s'_y) = N \quad (4)$$

which gives:

$$N \geq ceil(\|\vec{X}\|_2) \quad (5)$$

and ceil means integer rounding toward positive infinity and $\vec{a}, \vec{b}$ are mixing matrix unit vectors. The "abstract" data model (2) has physical interpretation when re-written in a form:

$$\begin{bmatrix} x_x \\ x_y \end{bmatrix} = \begin{bmatrix} \alpha J(\overline{\lambda}_x, T_x) & \alpha J(\overline{\lambda}_x, T_y) \\ \beta J(\overline{\lambda}_y, T_{y1}) & \beta J(\overline{\lambda}_y, T_y) \end{bmatrix} \begin{bmatrix} s_x \\ s_y \end{bmatrix} + \varepsilon \begin{bmatrix} s_x \\ s_y \end{bmatrix} \quad (6)$$

where $J(\overline{\lambda}_i, T_j)$, $i,j \in \{x,y\}$, represents blackbody radiation at temperature Tj in the band centered around wavelength $\lambda_i$ according to Planck's law:

$$J(\lambda, T) = \frac{2\pi hc^3}{\lambda^5 \left( \exp\left(\frac{hc}{k\lambda T}\right) - 1 \right)} \quad (7)$$

where c is speed of light, k is Boltzmann's constant, h is Planck's constant. α and β are constants representing CCD pixel gain and ϵ introduces small perturbation representing uncertainty level of the data model. $s_x$ and $s_y$ represent integral power of the sources the fractions of which are contained in sensor bands according to the blackbody radiation physics. Physics based data model (6) helps to estimated approximate values of the mixing angles in data model (2) as well as to estimate difference between them what will be important for the search algorithm described herein below.

Figure 8:
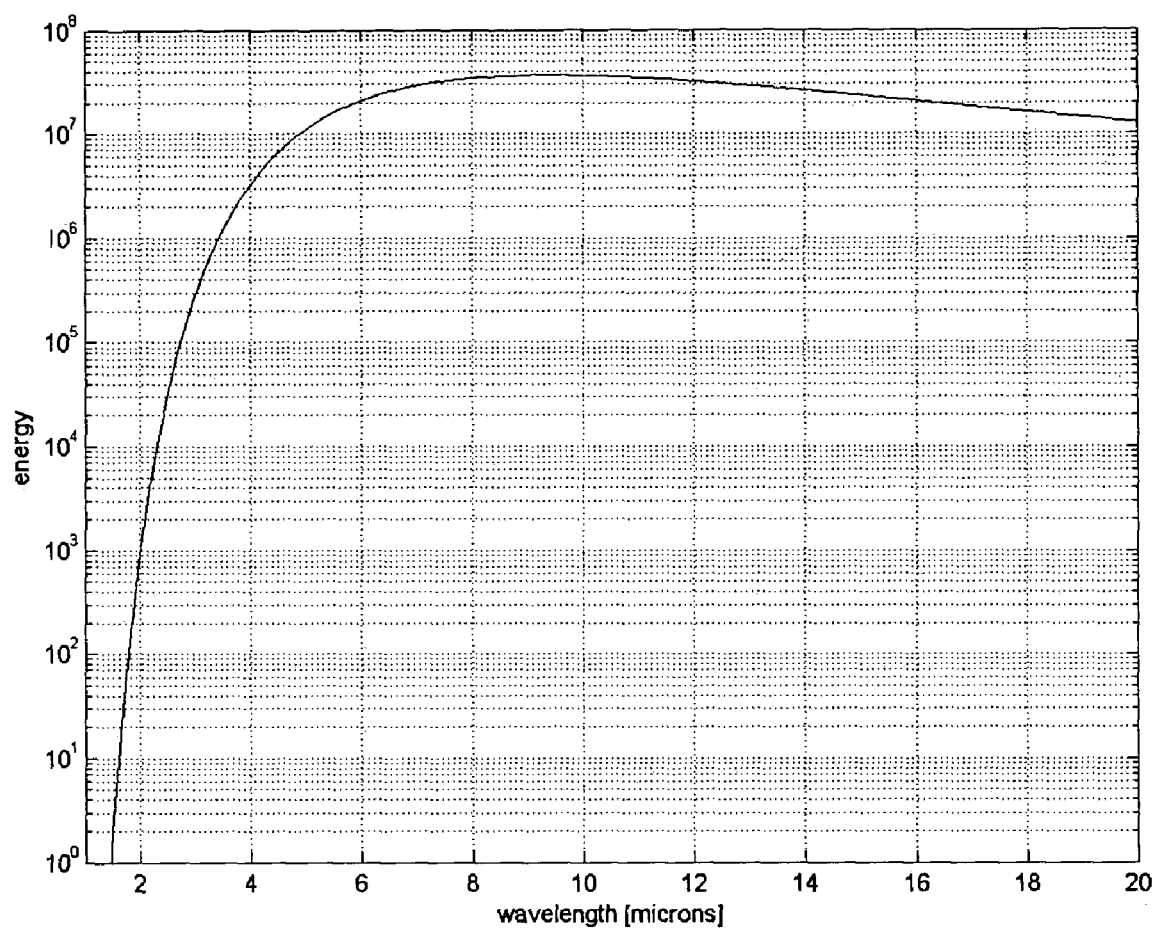
FIG. 8 is a blackbody radiation curve 800 based on the Planck's law between 0 and 20 μm for the temperature of 310° K. (37° C.), which is the temperature of the human body. The vertical axis is in the logarithm scale. The difference between in emanated energy level between short IR (3-5 μm) and long IR (8-12 μm) is approximately 3 orders of magnitude.

FIG. 8 is a blackbody radiation curve 800 based on the Plank's law between 0 and 20 μm for the temperature of 310° K. (37° C.), which is the temperature of the human body. The vertical axis is in the logarithmic scale. It can be seen that for a temperature of 310° K. peak, the radiation curve is between 8 and 10 μm (long IR wavelength). It can be also seen that energy level at 3 μm is approximately 1000 times smaller than at 9 μm.

If sensors suffer from nonlinear distortions the linear data model (2)/(6) has to be extended:

$$X_i^n = g(X_i), i \in \{x,y\} \quad (8)$$

where g( ) is the appropriate sensor nonlinearity with the unknown parameters. Then before applying linear LCNN algorithm data vector has to be linearized according to:

$$X_i = g^{-1}(X_i^n), i \in \{x,y\} \quad (9)$$

where $g^{-1}( )$ represents functional inverse of the sensor nonlinearity g( ) such that:

$$g^{-1} \circ g(X_i) = X_i, i \in \{x,y\} \quad (10)$$

and ∘ denotes composition of functions.

Figure 9:
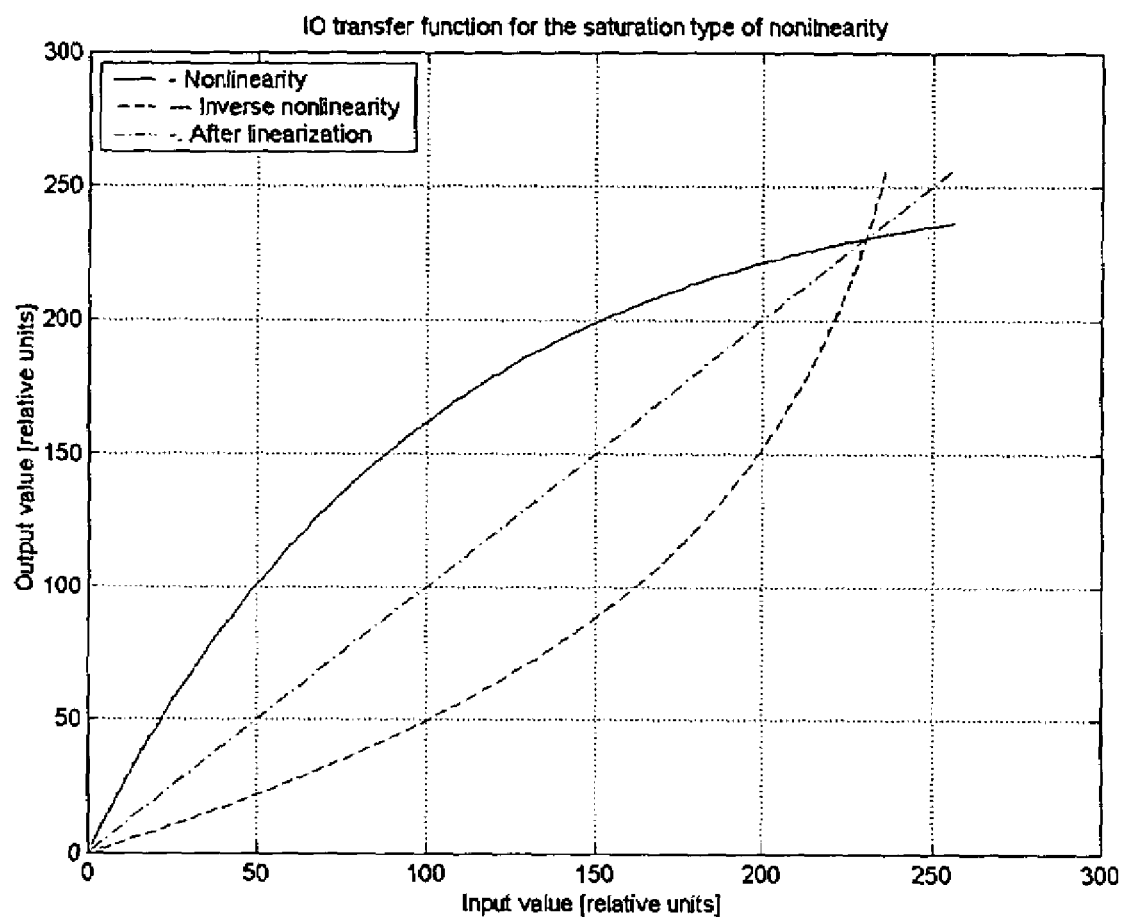
FIG. 9 is an Input-Output transfer function for saturation type of nonlinearity (solid line), for inverse nonlinearity (dashed line) and for ideally compensated nonlinearity (dashed dotted line) 900.

FIG. 9 is an Input-Output transfer function 900 for saturation type of nonlinearity (solid line), for inverse non-linearity (dashed line) and for ideally compensated nonlinearity (dashed dotted line).

FIG. 9 illustrates the linearization process for the nonlinear function:

$$g(x_i) = 2^B(1 - e^{-\alpha_i x_i}) \quad (11)$$

where B=8 represented number of bits and $\alpha_i$=0.01 is generally unknown parameter that controls slope of the nonlinearity (11). The nonlinear function (11) is shown by solid line in FIG. 9. Inverse of the nonlinear function (11) is based on (10) obtained as:

$$g^{-1}(x_i^n) = \frac{1}{\alpha_i} \ln \frac{1}{1 - \frac{x_i^n}{2^B}} \quad (12)$$

which for the given parameters B=8 and $\alpha_i$=0.01 is shown by dashed line in FIG. 9. Provided that generally unknown nonlinearity parameter $\alpha_i$ is perfectly estimated the composition of function g and $g^{-1}$ is gives linear function that is shown by dashed dotted line in FIG. 9. Based on the angle representation of the mixing matrix [A] in (2)/(6) the unmixing matrix [W] can be also represented in term of two killing angles as follows:

$$[W] = \frac{1}{\sin(\zeta - \xi)} \begin{bmatrix} \cos\xi & \sin\xi \\ \cos\zeta & \sin\zeta \end{bmatrix} = \begin{bmatrix} \vec{w}_1 \\ \vec{w}_2 \end{bmatrix} \quad (13)$$

where killing angles ξ,ζ are related to the mixing angles θ,ϕ through:

$$\xi = \varphi - \frac{\pi}{2} \quad (14)$$
$$\zeta = \theta + \frac{\pi}{2}$$

where due to the positivity constraints mixing angles θ,ϕ must sit in the first quadrant. Vectors of the unknown nonlinearity parameters $\vec{\alpha}$ and killing angles (ξ,ζ) as well as the magnitude of the source vector N are determined from the minimum of the absolute value of the Helmholtz free energy:

$$\min_{\vec{\alpha}, [W], N} |H + T_0 S| = \sqrt{\sum_{i=1}^{m} \left( \mu_i \left( \vec{w}_i g^{-1}(\vec{X}) - Ns'_i \right) \right)^2} \quad (15)$$

FIGS. 10A and 10B illustrate a property of the present invention to find the global minima of the error energy function (15) as a solution for the unknown nonlinearity slope parameter α and magnitude of the source vector N 1002 (FIG. 10A) as well as two killing angles perpendicular to the unknown mixing angles 1004 (FIG. 10B) by employing an exhaustive search method.

FIGS. 10A and 10B illustrate solution of the 4D optimization problem (15) for the unknowns (α,N,ξ,ζ) where it has been assumed that both sensors have the same value of the slope parameter $\alpha_x = \alpha_y = \alpha$. For the purpose of this simulation the nonlinear mixing problem has been given with:

$$\vec{X}'^n = g\left(\begin{bmatrix} \cos 64° & \cos 45° \\ \sin 64° & \sin 45° \end{bmatrix} \begin{bmatrix} 100 \\ 200 \end{bmatrix}\right) \quad (16)$$

$$= g\left(300x \begin{bmatrix} 0.4384 & 0.7071 \\ 0.8988 & 0.7071 \end{bmatrix} \begin{bmatrix} 0.3333 \\ 0.6666 \end{bmatrix}\right)$$

where the nonlinear function g in (15) has been given with (11) and with parameters B=8, α=0.01 In simulation shown in FIGS. 10A and 10B it has been assumed that slope parameter α has been changed ±10% around nominal value 0.01 i.e. α∈[0.99,0.011]. All four unknowns (α, N,ξ,ζ) have been found using exhaustive search strategy in the domain of support that for the killing angles is given with Eq.(14) and for the magnitude of the source vector with the inequality (5). FIG. 10A shows inverse of the error energy function (15) in the logarithmic scale in the (α, N) space. Unique solution (α*,N*)=(0.01,300) is associated with the global minimum the error energy function (15). For given pair (α*,N*)=(0.01,300) FIG. 10B shows inverse of the error energy function (15) in the logarithmic scale in the killing angle (ξ,ζ) space. For mixing angles (θ,ϕ)=(64°,45°) the optimal solution for the killing angles is, based on transformation (14), given with (ξ*,ζ*)=(154°,−45°) what is the case shown in FIG. 10B. Two solutions for angles ϕ and θ are consequence of the non-unique representation of the linearized data vector (2)/(6) i.e.:

$$\vec{X} = N(\vec{a}\,s'_x + \vec{b}\,s'_y) = N(\vec{b}\,s'_y + \vec{a}\,s'_x) \quad (17)$$

From the single pixel point of view this permutation is not a problem. From the space variant imaging point of view it could create problems because related components of two different source vectors corresponding with two different pixels could be assigned to two different images. However, the vector diagram in FIG. 7 shows that, depending on convention, for angles θ and ϕ it applies the following:

$$\phi \leq \chi \leq \theta \quad (18a)$$

or:

$$\theta \leq \chi \leq \phi \quad (18b)$$

where χ is angle defined from data vector $\chi = \tan^{-1}(x_y/x_x)$. Then adopting convention that angle ϕ is always greater than angle χ and that angle θ is always less than angle χ this type of permutation indeterminacy can be resolved for the space variant case. Adopted convention has physical interpretation in the context of multispectral IR imaging where feature vector corresponding with short IR radiation is always closer to the X axis. Discussed previously, a special case of the system design in which data vector X already represents source vector S is obtained by present invention when one mixing angle, say ϕ, is equal to 90° and another mixing angle, say θ, is equal to 0°.

Figure 11:
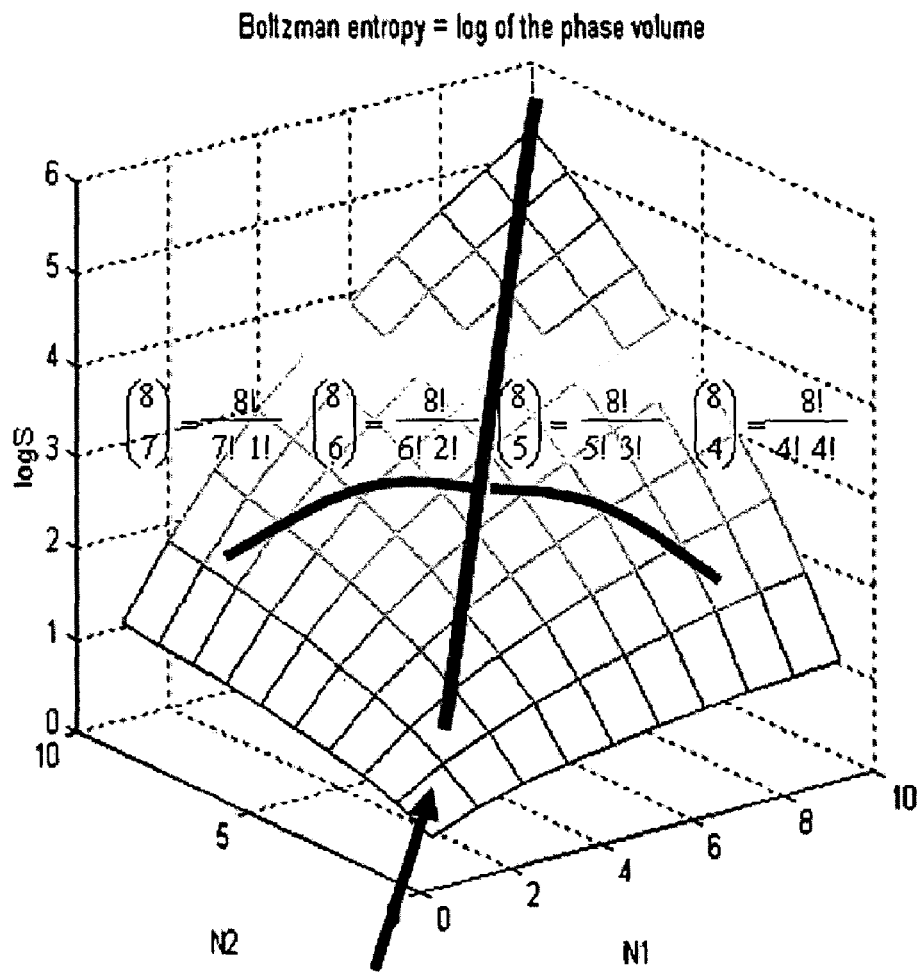
FIG. 11 shows the Shannon Entropy 1100 derived from Boltzmann Independent Phase Space.

FIG. 11 shows the Shannon Entropy derived from Boltzmann Independent Phase Space and with local convex surfaces, 1100, in which a local convex surface with 2I integers have I choices, e.g., 8=2×4 choices=(7+1, 6+2, 5+3, 4+4) and even positive integers 2I have local peaks entropy value at equal halves I.

The Shannon entropy S used in Eq.(15) is derived from the Boltzmann entropy shown in FIG. 11 and defined as $S_I = K_B \log V_I$, where each binomial expansion $$V_I \equiv \binom{8}{I} \equiv \frac{8!}{I!(8-I)!}; I = 0, 1, 2, \ldots 8,$$

uniquely produces step increases and decreases respectively of the components of data:

$$\binom{X_x + 1}{X_y - 1} = \begin{bmatrix} J & K \\ L & M \end{bmatrix} \binom{s_x - 1}{s_y + 1}; I = 0, 1, 2, 3, \ldots (s_x + s_y). \quad (19)$$

$$X_x = Js_x + Ks_y; \quad X_y = Ls_x + Ms_y$$

for a non-singular matrix: JM−KL≠0. Here, the Boltzmann entropy (which, amusingly, Boltzmann had engraved on his grave stone) gives the total number N of Red (R), Green (G), and Blue (B) color photons (e.g. in units of thousands): N=R+G+B. By means of Stirling's formula (logN!=NlogN−N), the combinatorial phase volume V=(N/R!G!B!) precisely gives the Shannon entropy formula:

$$S = K_B \log V = K_B \log\left(\frac{N!}{R!G!B!}\right) = -K_B N \sum_i s'_i \log s'_i \quad (20)$$

where the normalization by the magnitude of the source vector N yields the probability of the normalized source vector components:

$$H = E - T_0 S \quad (21)$$

$$= \vec{\mu}^T([W]\vec{X} - N\vec{S}') + NK_B T_0 \sum_{i=x,y} s'_i \log s'_i +$$

$$(\mu_0 N - NK_B T_0)\left(\sum_{j=x,y} s'_j - 1\right)$$

Figure 12:
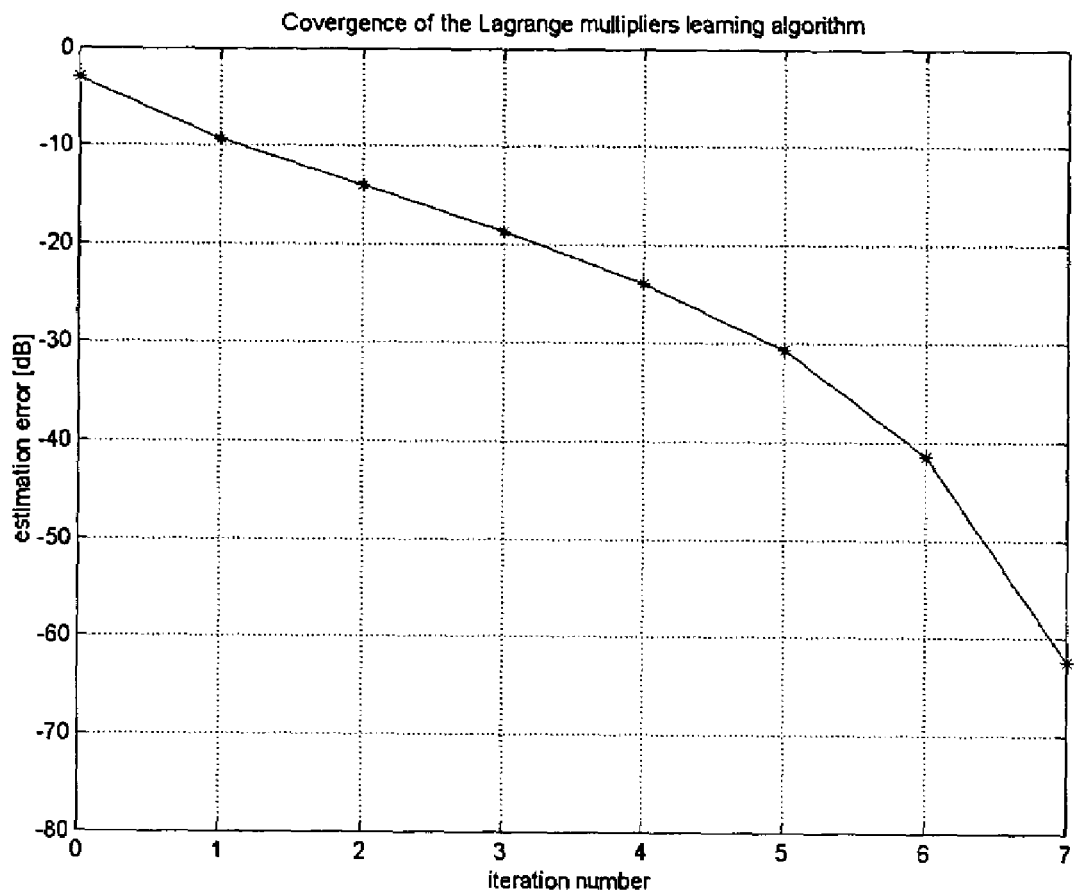
FIG. 12 shows present invention related convergence 1200 of the Lagrange multipliers $\vec{\mu}$ learning algorithm.

FIG. 12 shows present invention related convergence 1200 of the Lagrange multipliers $\vec{\mu}$ learning algorithm, Eq.(41a)-(41b). FIG. 12 shows error $|s'^*_x - s'_x|$ in dB as a function of the iteration index for the given optimal values of the parameters (α*,N*,ξ*,ζ*).

More particularly, FIG. 12 shows convergence of the Lagrange multipliers $\vec{\mu}$ learning algorithm (the single pixels, non-linear blind de-mixing algorithm of the present invention) which is derived herein below, in Eq.(29)-(41). FIG. 12 shows error $|s'^*_x - s'_x|$ in dB as a function of the iteration index for given optimal values of the parameters (α*,N*,ξ*,ζ*).

Figure 13:
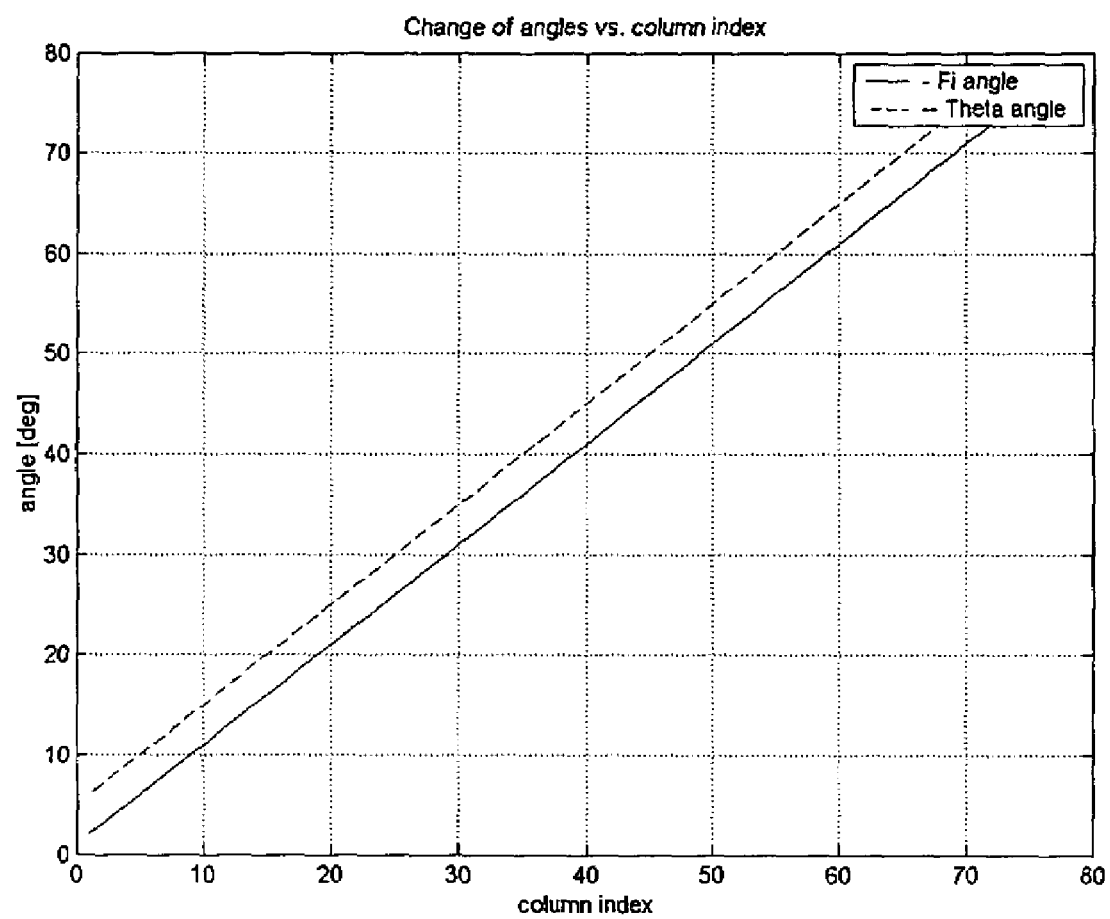
FIG. 13 shows a diagram of a column wise change of the mixing angles what implies space variant mixing 1300.

FIG. 13 shows a diagram 1300 of a column wise change of the mixing angles implies space variant mixing, in which the solid line—ϕ angle; and the dashed line—θ angle.

Two 72×88 images are now mixed by a mixing matrix that has been changed from pixel to pixel in order to simulate the space-variant imaging problem. Angles θ and ϕ are changed column wise according to FIG. 13 i.e. for every column index angles were changed for 1° and mutual distance between them is 4°.

Figure 14:
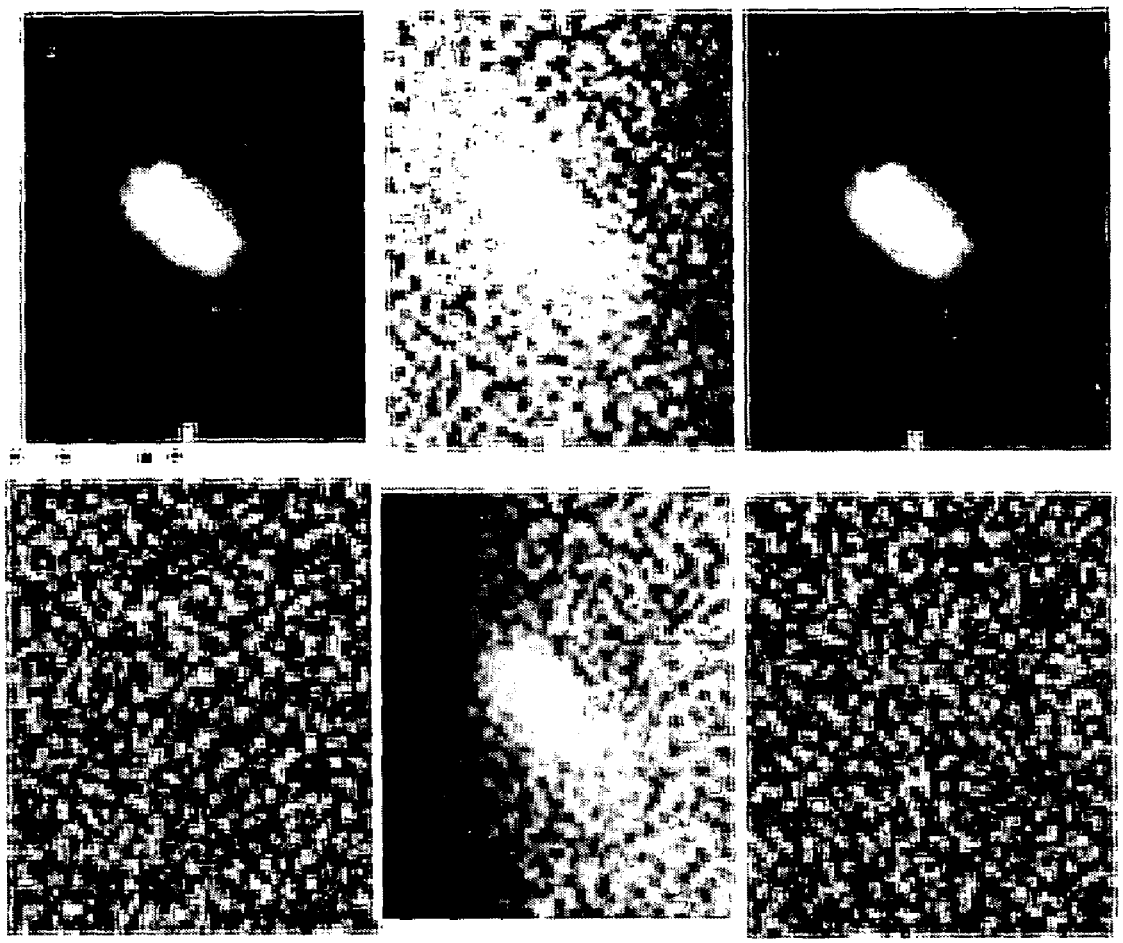
FIG. 14 shows that an application of the present invention is blind inversion of the space-variant nonlinear problem illustrated here on the example of imaging application.

FIG. 14 shows that an application of the present invention is blind inversion of the space-variant nonlinear problem illustrated here on the example of imaging application. From left to right: (i) source images that on accordance with adopted notation, Eq.(3) and (22), correspond with the vector S; (ii) space variant noise free nonlinear mixture that in accordance with the adopted notation, Eq.(3) and (22), correspond with vector X; (iii) source images recovered by the nonlinear LCNN algorithm (22)-(52) (the single pixel, non-linear blind de-mixing algorithm of the present invention) which again in accordance with the adopted notation, Eq.(3) and (22), represent recovered version of the vector S.

Results 1400 are presented in FIG. 14 which shows from left to right two source images, two images after linear mixture has been passed through nonlinearity (11) and two separated images using nonlinear LCNN algorithm (the single pixel, non-linear blind de-mixing procedure of the present invention) reported herein below. Since nonlinear LCNN algorithm solves the problem on the pixel-by-pixel basis the recovery is almost perfect although mixing matrix is space variant.

A fundamental aspect of the single pixel, non-linear blind de-mixing procedure of the present invention is given in the following three sections of mathematics which are embodied in the systems of the present invention.

This brain theory of learning is rigorously derived from the classical Statistical Mechanics (Stat-Mech). From it, the sigmoid threshold and Hebbian learning, etc. attributes of ANN Models, FIG. 15, were successfully derived. Moreover, the Stat-Mech had achieved for the first time the truly unsupervised learning of the brain intelligence without the need of an outside supervisor, FIG. 5.

Since the brain wet-ware could be considered merely as another classical many cellular body problem, it should be equally suited for the Stat-Mech treatment. The general theory of the present invention began with the laws of thermodynamics that correctly proclaimed about the inevitable death of any macroscopic system including life systems: "when the energy diffused, its entropy always increased". How could this law be utilized to model ANN? While the entropy increased, a data-constraint optimization achieved the balance. What would be the representation of data? The present invention assumed a local representation that permitted a linear matrix and vector algebra that could be generalized to nonlinear dynamical systems. Thus, the brain data $\vec{x}(t)$ is a vector time series represented the energy-excited state of arbitrary dimension N. The present invention asked for the underlying minimum redundancy sources $\vec{s}(t)$ of the dimension M that is unknown and equal to or less than N by the redundancy reduction Stat-Mech methodology.

$$\vec{x}(t) = \vec{g}([A]\vec{s}(t)) \qquad (22)$$

which gives:

$$\vec{s}(t) = [W]g^{-1}(\vec{x}(t)) \qquad (23)$$

where the unknown vector $\vec{g}(\circ)$ could be non-isotropic heat diffusion breast tissue function of the unknown sources $\vec{s}(t)$ or and $[W] \cong [A^{-1}]$. The linear expansion coefficient matrices [A] and [W] were also unknown and had to be determined by the thermodynamic equilibrium theory.

The mathematics of the blind inverse problem is peculiar and required the Stat-Mech skills when dealing with unknown or ill-defined matrix inversion algebra. Given the data vector, $\vec{x}(t)$ one had to invert the nonlinear matrix-vector Eq.(24) to find the most probable sources $\vec{s}(t)$ without knowing the coupling matrix [A]. Mathematically speaking, the equally probable distribution of the source components amounted to the maximum of the Shannon entropy:

$$S(\vec{s}\,') = -K_B N \Sigma_{i=1}^M s'_i \ln s'_i \qquad (24)$$

for equal distribution of components $$s'_i = \frac{1}{M}$$

that add up to equal to the probability one at the so-called MaxEnt heat death without giving any further information other than a total of M equally probable or non-redundant components. In Eq.(24) $K_B$ is the Boltzmann constant, and $\vec{s}\,'$ represents vector of normalized sources of the total strength $N = \Sigma_{i=1}^M s'_i$ i.e.:

$$s'_i = \frac{s_i}{N} \qquad (25)$$

Feedforward LCNN Unsupervised Learning

The single pixel, non-linear blind de-mixing procedure of the present invention is now explained.

Lacking of any other information, the vector of Lagrange multipliers $\vec{\mu}$ (known in mechanics as the virtual forces to stop the increase of the entropy) is multiplied with the estimation error $([W]g^{-1}(\vec{x}) - N\vec{s}\,')$ departed from the data (known as the virtual displacement):

$$E = \vec{\mu}^T ([W]g^{-1}(\vec{X}) - N\vec{s}\,') \qquad (26)$$

Then, any departure from the MaxEnt uniform distribution (heat death) is dictated by the measurement data $\vec{x}$ with the help of unsupervised learning matrix [W] and the Lagrange multipliers $\vec{\mu}$:

$$\min_{\vec{\alpha}, N, \vec{s}, [W], \vec{\mu}} H(\vec{s}, [W], \vec{\mu}) = E - T_0 S \qquad (27)$$

$$= \vec{\mu}^T ([W]g^{-1}(\vec{X}) - N\vec{s}\,') +$$

$$K_B T_0 \sum_{j=1}^M s'_j \ln s'_j +$$

$$N(\mu_0 - K_B T_0) \left( \sum_{j=1}^M s'_j - 1 \right)$$

where $\vec{\alpha}$ represents vector of the unknown nonlinearity parameters such as shown on FIG. 9. From the dimensionality analysis, if the Lagrange multiplier with the data is the energy, the entropy to be equivalent to the dimension of the energy must multiply the temperature $T_0$. The analytical solution for the class vector $\vec{s}$ is obtained by equating derivation of Helmholtz free energy $H(\vec{s}, [W], \vec{\alpha})$ with respect to $\vec{s}$ with zero:

$$\frac{\partial H}{\partial s'_j} = \frac{\partial E}{\partial s'_j} - T_0 \frac{\partial S}{\partial s'_j} = -\mu_j N + K_B T_0 N \ln s'_j + \mu_0 N = 0 \quad (28)$$

$$s'_j = \exp\left(\frac{\mu_j - \mu_o}{K_B T_0}\right) \quad (29)$$

That the real positive Eq. (28) is indeed the minimum of H is verified because of:

$$\frac{\partial^2 H}{\partial^2 s_j} = K_B T_0 \frac{1}{s_j} \geq 0 \quad (30)$$

and due to the (27) minimum of H implies maximum of S. The right hand side of Eq. (29) is called the canonical ensemble partition function Z in the Stat-Mech. The unknown message $\vec{s}$ is normalized by the probability i.e. weighted by the partition function Eq. (29) as follows:

Theorem: Sigmoid Threshold for Optimum Communication

Any unknown message $\vec{s}$ defined by the Lagrange Constraint Helmholtz free energy $$\min_{\vec{\alpha}, \vec{s}, [W]} H(\vec{s}, [W]) = E - T_0 S$$

had real positive monotonic sigmoid threshold logic.

Proof. It follows from Eqs.(27-29)

$$\sum_{j=1}^{M} s'_j = \sum_{j=1}^{M} \exp\left(\frac{1}{K_B T_0}\mu_j - \frac{\mu}{K_B T_0}\right) = 1 \quad (31)$$

$$s'_j = \exp\left(\frac{1}{K_B T_0}\mu_j\right) \Big/ \sum_{k=1}^{M} \exp\left(\frac{1}{K_B T_0}\mu_k\right)$$

$$= \frac{1}{1 + \sum_{\substack{k=1 \\ k \neq j}}^{M} \exp\left[\frac{1}{K_B T_0}(\mu_k - \mu_j)\right]} = \sigma_j(\vec{u})$$

Bipolar version of the threshold logic is simply a scale up version $s_j^\pm = 2s_j - 1$. This sigmoid form is universal in biology and in communication theory.

Figure 15:
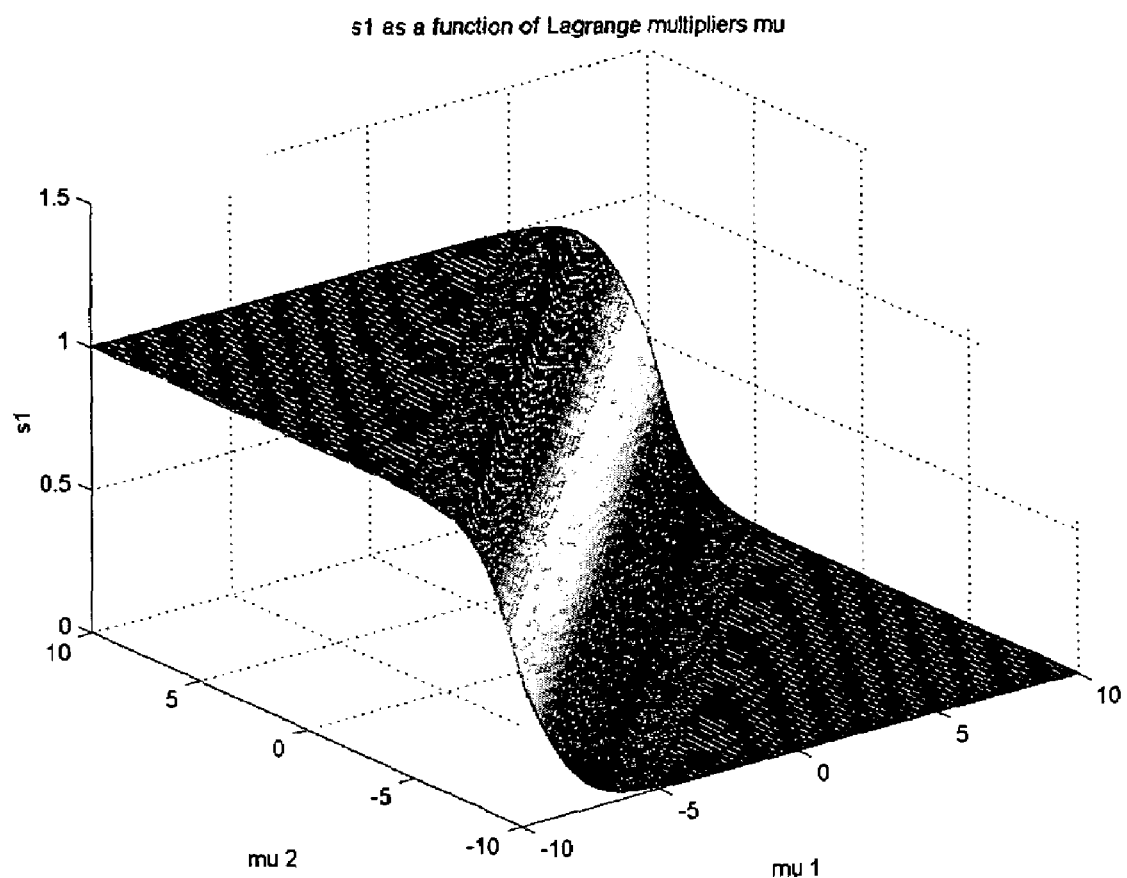
FIG. 15 is the present invention related vector sigmoid transfer function $s_1=\sigma_1(\vec{\mu})$ 1500 for a 2-D version.

FIG. 15 is the present invention related vector sigmoid transfer function $s_1 = \sigma_1(\vec{\mu})$ 1500 for a 2-D version of Eq.(31). FIG. 15 shows 2-dimensional (2-D) cross section view of the sigmoid behavior 1500 from the constraint $\vec{\mu}$-nodes to the message $\vec{s}$-nodes.

Theorem: Variation of thermodynamic free energy $\mu_0$ with respect to virtual Lagrange constraint forces $\mu_j$ gives displacement of virtual sources $s'_j$.

Proof: Imposing the constraint of probability normalization condition $\Sigma_{j=1}^M s'_j = 1$ and using Eq.(29) the partition function of the canonical ensemble in Statistical Mechanics is obtained:

$$\exp\left(\frac{\mu_0}{K_B T_0}\right) = \sum_{j=1}^{m} \exp\left(\frac{\mu_j}{K_B T_0}\right) \equiv Z \quad (32)$$

From (32) the relation between the free energy $\mu_0$ and virtual forces $\mu_j$ satisfies:

$$\frac{\partial \mu_0}{\partial \mu_j} = s'_j \quad (33)$$

Q.E.D.

Theorem: Equilibrium Learning Rule for Lagrange Multipliers.

Virtual Lagrange forces $\mu_j$ are changed in the direction of minimal displacement from data.

Proof. Using the perturbation theory the iterative update rule for the Lagrange multipliers with respect to data error is derived as:

$$\Delta \mu_j = \sum_{i=1}^{m} \frac{\partial \mu_j}{\partial s'_i} \Delta s'_i \quad (34)$$

After partial integration of Eq.(33) yields:

$$\mu_{0j}^{(k+1)} = \mu_{0j}^{(k)} + \int_k^{k+1} \frac{\partial \mu_0}{\partial \mu_j} d\mu_j = \mu_{0j}^{(k)} + s_j^{(k)} \Delta \mu_j \quad (35)$$

Adding $\mu_{0j}^{(k+1)}$ together yields:

$$\mu_0^{(k+1)} = \sum_{j=1}^{M} \mu_{0j}^{(k+1)} = \mu_0^{(k)} + \sum_{j=1}^{M} s_k'^{(k)} \Delta \mu_j \quad (36)$$

$$= \sum_{j=1}^{M} s_j'^{(k)} \mu_j^{(k+1)} + C$$

where C is integration constant defined as:

$$C = \mu_0^{(k)} - \Sigma_{j=1}^{M} s_j'^{(k)} \mu_j^{(k)} \quad (37)$$

It follows from Eq. (29):

$$\mu_j = K_B T_0 \log s'_j + \mu_0 \quad (38)$$

Now from (38) and (39) it follows:

$$\frac{\partial \mu_j}{\partial s_j} = \frac{\partial \mu_j}{\partial s'_j} \frac{ds'_j}{ds_j} = \frac{K_B T_0}{N} \frac{1}{s_j'^{(k)}} + \frac{1}{N} \frac{\partial \mu_0}{\partial s_j'^{(k)}} = \frac{K_B T_0}{N} \frac{1}{s_j'^{(k)}} + \frac{\mu_j^{(k)}}{N} \quad (39)$$

and:

$$\frac{\partial \mu_j}{\partial s_i} = \frac{\partial \mu_j}{\partial s'_i} \frac{ds'_i}{ds_i} = \frac{1}{N} \frac{\partial \mu_0}{\partial s'_1} = \frac{1}{N} \mu_i^{(k)} \quad (40)$$

Finally expression for update of the Lagrange multipliers is obtained as:

$$\Delta \mu_j = \sum_{i=1}^{m} \frac{\partial \mu_j}{\partial s_i'} \Delta s_i' \qquad (41a)$$

$$= \left(\frac{K_B T_0}{s_j'^{(k)}} + \mu_j^{(k)}\right)\left(\vec{w}_j^{(l)} g^{-1}(\vec{X}) - N^{(l)} s_j'^{(k)}\right) +$$

$$\sum_{\substack{i=1 \\ i \neq j}}^{M} \mu_i^{(k)}\left(\vec{w}_i^{(l)} g^{-1}(\vec{X}) - N^{(l)} s_i'^{(k)}\right)$$

$$\mu_j^{(k+1)} = \mu_j^{(k)} + \Delta \mu_j \qquad (41b)$$

Q.E.D.

Theorem: Initial conditions for MaxEnt like algorithm (the single pixel, non-linear blind de-mixing procedure of the present invention). In the absence of any knowledge most fair assumption for the source probabilities $s'_j$ is the Maximum Entropy assumption $$s_j'^{(0)} = \frac{1}{M}$$

with the zero initial value of the virtual forces $\mu_j^{(0)} = 0$.

Proof. Assuming maximum entropy initial conditions for the source probabilities:

$$s_j' = \frac{1}{M} \qquad (42)$$

from Eq.(29) yields:

$$\exp\left(\frac{\mu_j^{(0)}}{K_B T_0}\right) = \frac{1}{M} \exp\left(\frac{\mu_0^{(0)}}{K_B T_0}\right) \qquad (43)$$

and from Eq.(32):

$$\exp\left(\frac{\mu_0^{(0)}}{K_B T_0}\right) = \sum_{j=1}^{M} \exp\left(\frac{\mu_j^{(0)}}{K_B T_0}\right) \qquad (44)$$

Combining Eq.(43) and (44) yields:

$$M \exp\left(\frac{\mu_j^{(0)}}{K_B T_0}\right) = \sum_{k=1}^{M} \exp\left(\frac{\mu_k^{(0)}}{K_B T_0}\right) \qquad (45)$$

that is satisfied for:

$$\mu_j^{(0)} = 0 \; \forall j \in \{1, \ldots, M\} \qquad (46)$$

Inserting (46) into (44) yields:

$$\mu_0^{(0)} = K_B T_0 = \log M \qquad (47)$$

and inserting (47) into (43) yields:

$$\exp\left(\frac{\mu_j^{(0)}}{K_B T_0}\right) = 1$$

from which it follows:

$$\mu_j^{(0)} = 0$$

what is verification of the virtual force initial condition (46). Q.E.D.

Theorem: Global minimum of the absolute value of the Helmholtz free energy. Vector of the unknown nonlinearity parameters $\vec{\alpha}$, de-mixing matrix $[W]$ and source magnitude $N$ are determined at the minimum of the absolute value of the Helmholtz free energy (27).

Proof. Because the Shannon entropy $S$ in Eq.(27) is a convex function that does not depend on the nonlinearity parameters $\vec{a}$, de-mixing matrix $[W]$ and scaled parameter $N$ one could add it to Eq. (27), yielding:

$$\min_{\vec{\alpha},[W],N} |H + T_0 S| \cong \min_{\vec{\alpha},[W],N} |H| \cong \min_{\vec{\alpha},[W],N} |E| \qquad (48)$$

$$= \sqrt{\sum_{i=1}^{m} \left(\mu_i\left(\vec{w}_i g^{-1}(\vec{X}) - N s_i'\right)\right)^2}$$

which shows that minimization of the data error energy $|E|$ w.r.t. triplet $(\vec{\alpha},[W],N)$ is equivalent to the minimization of the Helmholtz free energy $|H|$ w.r.t. $(\vec{\alpha},[W],N)$. The initial value of the unknown scaling constant $N = \sum_{j=1}^{m} s'_j$ is estimated from data vector $\vec{X}$ based on the triangle inequality $\|\vec{X}\|_2 \leq N \sum_{j=1}^{m} \|\vec{a}_j\|_2 s'_j$ and assuming unit column L2 norm of the mixing matrix $[A]$ it becomes:

$$\|\vec{X}\|_2 \leq N \qquad (49)$$

At some iteration/output triplet $(\vec{\alpha}^{(l)},[W]^{(l)},N^{(l)})$ is generated as an output of the optimization algorithm in an attempt to reach possibly global minimum of the estimation error energy (27)/(48). For a given triplet $(\vec{\alpha}^{(l)},[W]^{(l)},N^{(l)})$ the MaxEnt like algorithm (29)-(48) computes the most probable solution for the source vector $\vec{S}^{(l)} = N^{(l)} \vec{S}'^{(l)}$. This represents feedback for the optimization algorithm that computes a new value of the estimation error energy and generates a new triplet $(\vec{\alpha}^{(l+1)},[W]^{(l+1)},N^{(l+1)})$. After each iteration I is completed a quadruple $(\vec{\alpha}^{(l)},[W]^{(l)},N^{(l)},\vec{S}'^{(l)})$ is obtained. The single pixel, non-linear blind de-mixing algorithm of the present invention accepts as a final solution the quadruple $(\vec{\alpha}^*,[W]^*,N^*,\vec{S}'^*)$ for which the estimation error energy (27)/(48) reaches a possibly global minimum. Provided that nonlinear function $g()$ has unique inverse the quadruple $(\vec{\alpha}^*,[W]^*,N^*,\vec{S}'^*)$, corresponding with given data model (22), will give a global minimum of the error energy function. This is because for a given triplet $(\vec{\alpha}^*,[W]^*,N^*)$ the MaxEnt like algorithm (29)-(41) converges toward $$\vec{S}'^* = \frac{\vec{S}^*}{N^*}$$

and for triplet ($\vec{\alpha}^*$,[W]*,N*) the error energy function becomes (48):

$$|E(\vec{\alpha}^*,[W]^*,N^*)|=|[W]^*g^{-1}(\vec{\alpha}^*,\vec{X})-N^*\vec{S}'^*| \quad (50)$$

because by assumption g( ) has unique inverse $g^{-1}$ ($\vec{X}$)=[A]*$\vec{S}$* only when $\vec{\alpha}=\vec{\alpha}$*. Then due to the fact that [W]*=([A]*)$^{-1}$ and $\vec{S}$*=N*$\vec{S}'$* the error energy function (21) becomes:

$$|E(\vec{\alpha}^*,[W]^*,N^*)|=|\vec{S}^*-N^*\vec{S}'^*| \quad (51)$$

Q.E.D.

Theorem of Unsupervised Hebb Rule: Update of the Inverse of the Associative Memory (AM) Matrix is done by means of metric-weighted gradient descent of LCNN.

Proof. The learning rule for the inverse of the associative memory matrix from the Lagrange Constraint Minimum Helmholtz Free Energy at the single pixel level is derived in the present invention as:

$$\frac{\partial[W]}{\partial t} = -\left\langle\frac{\partial H(\vec{s},[W])}{\partial[W]}\right\rangle_{\vec{s}} \quad (52)$$

$$[W(k+1)] = [W(k)] + \Delta t \partial[W]/\partial t$$
$$= [W(k)] - \Delta t \langle \partial H(\vec{s},[W])/\partial[W]\rangle_{\vec{s}}$$
$$= [W(k)] - \Delta t \vec{\mu}\vec{x}^T$$

where $\Delta t$ is the infinitesimal time increment, k the iteration index and $\vec{\mu}$ the Lagrange multipliers and the subscript $\vec{s}$ meant the ensemble average that explained why the stochastic gradient is done pixel by pixel independently and did not need to scramble the neighborhood data. Q.E.D.

The gradient descent learning rule (52) is useful substitution for the exhaustive search algorithm associated with the minimization of the error energy function (48) when initial value of the de-mixing matrix is chosen close enough to the global minimum of the error energy function (48).

Figure 16:
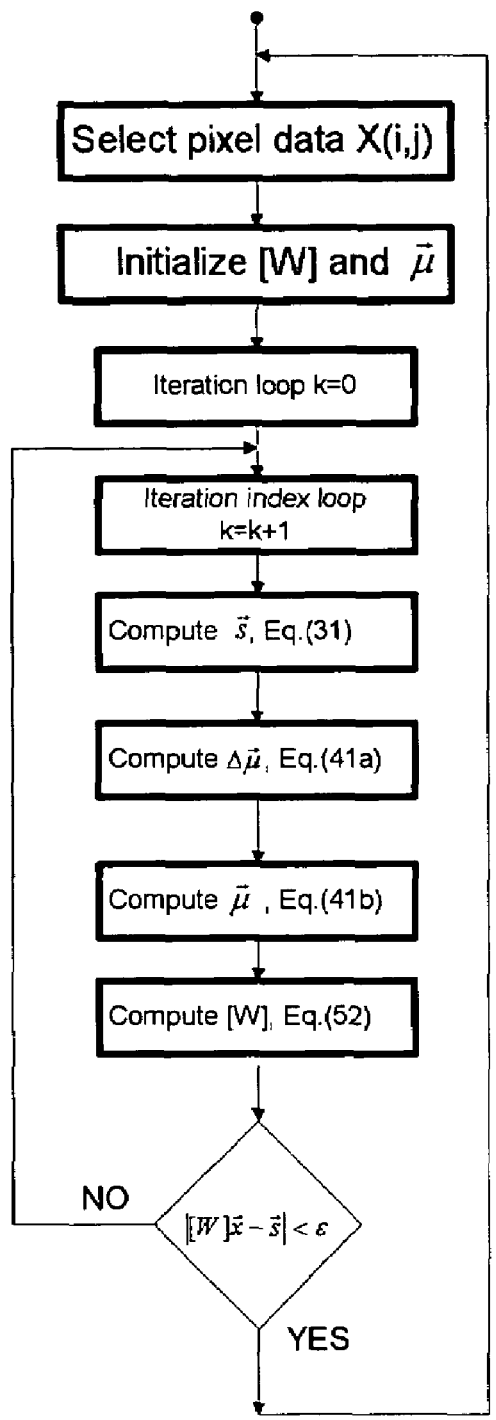
FIG. 16 is the present invention related flow-chart diagram 1600 of the nonlinear feedforward LCNN (the single pixel, non-linear blind de-mixing procedure of the present invention).

FIG. 16 is the present invention related flow-chart diagram 1600 of the nonlinear feedforward LCNN (the single pixel, non-linear blind de-mixing procedure of the present invention), Eq.(22)-(52), suitable to implement on a digital signal processor (DSP) or Field Programmable Gate Array (FPGA). That is, the flow-chart diagram of the feedforward LCNN, Eq.(22)-(52) (the single pixel, non-linear blind de-mixing procedure of the present invention), suitable for implementation on Digital Signal Processor (DSP) is shown on FIG. 16.

Referring now to FIG. 16, pixel data is selected X(I,j). Next, vectors are initialized. Then, an iteration loop k=0. Next, an iteration index loop k=k+1 is set. Equation (31) is then executed, followed by Equation (41a), Equation (41b), and Equation (52). The procedure 1600 is repeated if the final parameter is not met.

The single unit circuit diagram of the feedforward LCNN, Eq.(22)-(52) (the single pixel, non-linear blind de-mixing procedure of the present invention) which is suitable for scalable implementation on mixed (analog and digital) VLSI circuits is shown in FIG. 17.

FIG. 17 is a present invention related single unit circuit diagram 1700 of the feedforward LCNN method (the single pixel, non-linear blind de-mixing method of the present invention), Eq.(12)-Eq.(29), with a description of computational processes given in FIG. 19. By using one switch (SW1) the network can compute vector summation: $\Sigma_{j=1}^N w_{ij} x_j$ and necessary to compute update of the Lagrange multipliers $\vec{\mu}$. Each element of the feedforward un-mixing matrix [W] is updated locally. The described computational unit 1700 is suitable for scalable implementation on both analog and digital VLSI circuits.

A description of computational processes of the single pixel, non-linear blind de-mixing procedure of the present invention is shown in FIG. 18. FIG. 18 shows a description of computational processes of the present invention for the single unit circuit diagram 1700 shown in FIG. 17, of the linear feedforward LCNN method (the single pixel, non-linear blind de-mixing method of the present invention), Eq.(22)-Eq.(52).

As shown in FIG. 18, 1.) relates to SW1 opened, 2.) relates to SW1 closed, 3.) relates to updating the unmixing matrix [W] locally, 4.) relates to SW1 closed, 5.) relates to SW1 closed, 6.) relates to computing the partition function Z, 7.) relates to computing locally source components, and 8.) returns to 1.).

FIG. 19 shows the present invention related feedforward LCNN (single pixel, non-linear blind de-mixing of the present invention) circuit diagram 1900 for a general N-D case. FIG. 19 indicates a massively distributed equivalent circuit 1900. The feedforward LCNN (single pixel, non-linear blind de-mixing of the present invention) shown in FIG. 19 could be implemented in VLSI circuits 2100 as illustrated on FIG. 21.

More particularly, a circuit diagram 1900 of the complete feedforward LCNN (the single pixel, non-linear blind de-mixing procedure of the present invention) for a 3-dimensional (3-D) case is shown in FIG. 19.

FIG. 20 is a present invention related illustration of the two-stage deterministic feed-forward blind-source separation algorithm (the single pixel, non-linear blind de-mixing algorithm of the present invention) 2000 where first stage 2002 includes linearization or rectification of the nonlinear data vector $\vec{X}$ and second stage 2004 includes application of the linear LCNN algorithm Eq.(1)-(52) on the linearized or rectified data vector. The linear LCNN algorithm (the linear version of the single pixel, non-linear blind de-mixing algorithm of the present invention) assumes the linearity condition $g(x_i)=x_i$ is satisfied and is obtained as a special case of the more general nonlinear LCNN algorithm.

The feedforward LCNN (the single pixel, non-linear blind de-mixing procedure of the present invention) shown in FIG. 19 could be implemented in VLSI circuits as illustrated in FIG. 20.

FIG. 21 illustrates how the feedforward LCNN (the single pixel, non-linear blind de-mixing algorithm of the present invention) shown on FIGS. 16-19 represents a scalable solution for a 0.25 µm VLSI implementation. As shown in FIG. 21, a system 2100 implementing the single pixel, non-linear blind de-mixing algorithm of the present invention includes a system integration module, a digital signal processing (DSP) chip 2102, and mixed-signal chip 2104, DSP Firmware, Fitting software, a DSP implementation of the single pixel, non-linear blind de-mixing algorithm of the present invention, and implementation of the science of unsupervised signal separation.

Application of the Present Invention to Medical Systems

The present invention includes all conceivable applications that are enabled by means of the elucidation and teaching of the human brain sensor pairs through the unsupervised learning by the single pixel, non-linear blind de-mixing procedure of the present invention (that is, the Nonlinear Lagrange Constraint Neural Network (Nonlinear LCNN)).

The present invention is related to the use of pairs of smart sensors/instruments for diagnoses passively and actively, in glass, in bio-tissue, in channels. More specifically it is accomplished by passively detecting thermal changes in the body fluids flow by using the single pixel, non-linear blind de-mixing procedure of the present invention applied to unsupervised fusion of sensor pairs but can be extended to more general biomedical measurement and diagnoses instruments. Applications are demonstrated and illustrated in the breast cancer detection, FIG. 22, multi-mode fiber optics imaging, FIG. 23, and the binaural hearing aids, FIG. 24.

In the light of the above teachings obviously many modifications and variations of the present invention are possible. It is therefore to be understood that, within the scope of the appended claims, the invention many be practiced otherwise than as specifically described.

More specifically the single pixel, non-linear blind de-mixing procedure of the present invention (that is, the unsupervised algorithm) is applied to the breast cancer detection problem using passive two-color infrared imaging. Application of the same methodology can be extended to passively detect blockages in the human body fluid circulatory system. Other biomedical applications of the algorithm of the present invention include in situ data gathering or imaging using multiple mode fiberoptical sensing as well as selective amplification hearing aids through two-ear binaural processing for de-noise echo cancellation and signal classification. Of special interest is also the capability of the present invention to detect virtual tumor generated as a consequence of the reflected fluorescent light of the artificial reference source such as in multiple mode fiberoptical sensing.

The present invention accomplishes simultaneous fusion and classification of several IR breast images based on the human brain pairs sensor unsupervised learning, using the single pixel, non-linear blind de-mixing procedure of the present invention, as shown in FIG. 22.

FIG. 22 shows the present related two-spectral single optical axis breast imaging system 2200 which enables more accurate pre-cancer ductal carcinoma in situ (DCIS) tumor classification and diagnosis than standard single color breast imaging or X-ray based mammography. More particularly, the system 2200 includes a multispectral IR camera 2202 which takes an image of the (1) Right breast, with (2) a two-color IR camera, and separates the image by a beam splitter and two-charge-coupled devices (CCD1 and CCD2 each detecting a beam of a different wavelength) into a (3) first IR band breast image, first component of the data vector X in models (3)/(22); and (4) a second IR band breast image, second component of the data vector X in models (3)/(22). The system 2200 also includes a (5) Computer 2204 with implemented feedforward LCNN algorithm (that is, executing the single pixel, non-linear blind de-mixing procedure of the present invention) to produce a (6) first de-mixed breast image containing cancer for example, first component of the source vector S in models (3)/(22) and a (7) second de-mixed breast image containing healthy tissue for example, second component of the source vector S in models (3)/(22).

The concept of angiogenesis as suggested by Gamagami (Gamagami P, "Indirect signs of breast cancer," Angiogreneis study. In: *Atlas of Mammography*, Cambridge, Mass., Blackwell Science, pp, 231-258, 1996) as an integral part of an early breast cancer, is of key importance for understanding the success of the single pixel, non-linear blind de-mixing procedure of the present invention (the brain-like smart sensors pair unsupervised LCNN algorithm) to detect breast cancer as a class which is different from the healthy tissue. His concept was reiterated in 1996 by Guido and Schnitt (Guidi A. J., and Schnitt S. J., "Angiogenesis in preinvasive lesions of the breast," *The Breast J* 2: 364-369, 1996), whose observations suggested that angiogenesis is an early event in the development of breast cancer. They noted that it might occur before tumor cells acquired the ability to invade the surrounding stoma and even before there was morphologic evidence of a ductal carcinoma in situ (DCIS). Anbar (Anbar M, "Hyperthermia of the cancerous breast: Analysis of mechanism," *Cancer Lett.* 84: 23-29, 1994; Anbar M., "Breast cancer," in: *Quantitative Dynamic Telethermometry in Medical Diagnosis and Management*. Ann Arbor, Mich.: CRC Press, pp. 84-94, 1994), using an elegant biochemical and immunological cascade, suggested that the empirical observation that small tumors capable of producing notable IR changes could be due to enhanced perfusion over a substantial area of breast surface via tumor-induced nitric oxide vasodilatation. That enables the single pixel, non-linear blind de-mixing procedure of the present invention based on a multiple color IR sensory system to classify a tumor from healthy tissue that can be 1 mm in diameter and which can help to detect cancers that are not visible through mammography that was already shown for standard single-camera based thermography (Head J. F., Wang F., and Elliott R. L., "Breast thermography is a noninvasive prognostic procedure that predicts tumor growth rate in breast cancer patients," *Ann NY Acad Sci* 698:153-158, 1993).

The two-color camera is designed to operate in the long IR band between 8 and 12 µm. In that band physics of the blackbody radiation described in (equation) data model (6) will enable angular separation between mixing angles of the order of 0.1° for the two objects with temperature difference of 0.1° K. with the absolute temperature of 310° K. Because at given temperature the blackbody radiation is maximal in the band between 8 and 12 µm this will give maximal signal level to the detector. In order to maximize signal-to-noise ratio camera must be cooled to minimize dark current level. In this regard, the quantum well IR photodetectors are very promising technology long IR detectors due to the property of the quantum well detectors to narrow bandgap of the detector without having to deal with the poor properties of narrow-gap semiconductors. This enables low-energy long IR photons (8 and 12 µm) to generate significantly more currents i.e. to increase efficiency. Because dark current level is governed by temperature this reduces cooling requirements on the quantum-well detectors that operate in the region between 8 and 9 µm. Consequently, cooling at the refrigerator level could be enough to compensate for dark current effect.

Following the logic of the angiogenesis concept, which due to the enhanced perfusion over a substantial area of breast surface via tumor-induced nitric oxide vasodilatation enabled early breast cancer detection as a class which is different from healthy tissue, the single pixel, non-linear blind de-mixing procedure of the present invention can be applied to passively detect blockages in the body fluid circulatory system as well.

In situ fiberoptical data gathering or imaging devices using the single pixel, non-linear de-mixing procedure of the present invention are accomplished using the embodiment of the multiple mode fiber optical for multiple sensing as illustrated in FIG. 23.

FIG. 23 shows an optical layout of a dual-mode fiberoptic endoscope system 2300 of the present invention, including; (1) biological tissue; an image acquisition system 2302 including (2) an objective lens; (3) a dual-mode fiber; (4) an ocular lens; (5) a detector array at the wavelength $\lambda_1$, first component of the data vector X in models (3)/(22); (6) a detector array at the wavelength $\lambda_2$, second component of the data vector X in models (3)/(22); (7) and a computer 2304 with implemented feedforward LCNN algorithm (the single pixel, non-linear blind de-mixing procedure of the present invention); (8) first de-mixed tissue image, first component of the source vector S in models (3)/(22); (9) second de-mixed tissue image, seconds component of the source vector S in models (3)/(22).

As shown in FIG. 23, an image of the tissue (1) is presented by the ocular lens (2) to the Dual-mode fiber relay (3), which transmits the image to the ocular lens (4). The ocular lens (4) focuses the image on the scanning mirror, which divides the image by wavelength onto a first detector array (5) and a second detector array (6). The detector arrays, in one embodiment being charge coupled devices, transfer the detected images to the computer 2304, data vector X in models (3)/(22). The computer 2304 executes the LCNN unsupervised two-spectral image classification algorithm, which corresponds to the single pixel, non-linear blind de-mixing procedure of the present invention, to acquire de-mixed images (8) and (9) and identify the heat source presented therein, source vector S in models (3)/(22).

Following the same logic as in the case of breast cancer detection the multiple modes fiber-optic enables the single pixel, non-linear de-mixing procedure of the present invention to perform unsupervised classification of the multispectral image of the biological tissue.

Selective amplification hearing aids of the related art are based on a single inner ear cochlear mechanism. A binaural property had yet not found its way into the design of modern hearing aids because the industry is lacking of an unsupervised learning algorithm and implementation devices until the single pixel, non-linear blind de-mixing procedure of the present invention which enables a "binaural selective amplifier" with the help of the wireless chip (spread spectrum at short range at 3.4 GHz called "Bluetooth", or home appliance, or IEEE standard) and fast processor chip of a POCKET PC (PALM PILOT, etc). The present invention includes de-noise echo cancellation and signal classification simultaneously taking advantage of two-ear binaural processing and the single pixel, non-linear blind de-mixing procedure (smart unsupervised nonlinear feedforward LCNN algorithm) of the present invention, as shown in FIG. 24.

FIG. 24 shows a selective amplification hearing aids system 2400 by means of two ears-like binaural nonlinear feedforward LCNN signal processing (the single pixel, non-linear blind de-mixing procedure of the present invention) including (1) a two-microphone sensory system 2402, data vector X in models (3)/(22); (2) a nonlinear unsupervised feedforward LCNN algorithm (the single pixel, non-linear blind de-mixing procedure of the present invention implemented as a non-linear LCNN unsupervised signal from noise separation system by a computer) 2404; (3) PDA-like device with a DSP executed nonlinear feedforward LCNN algorithm (the single pixel, non-linear blind de-mixing procedure of the present invention) 2406; which (4) extracts noise from the recorded signal, first component of the source vector S in models (3)/(22); and transmits (5) clear signal by a wireless system to the selective hearing amplifier 2408, second component of the source vector S in models (3)/(22).

Having described the invention, the following examples are given to illustrate specific applications of the invention including the best mode now known to perform the invention. These specific examples are not intended to limit the scope of the invention described in this application.

An example of the application of the single pixel, non-linear blind de-mixing procedure of the present invention is now presented.

Figure 1:
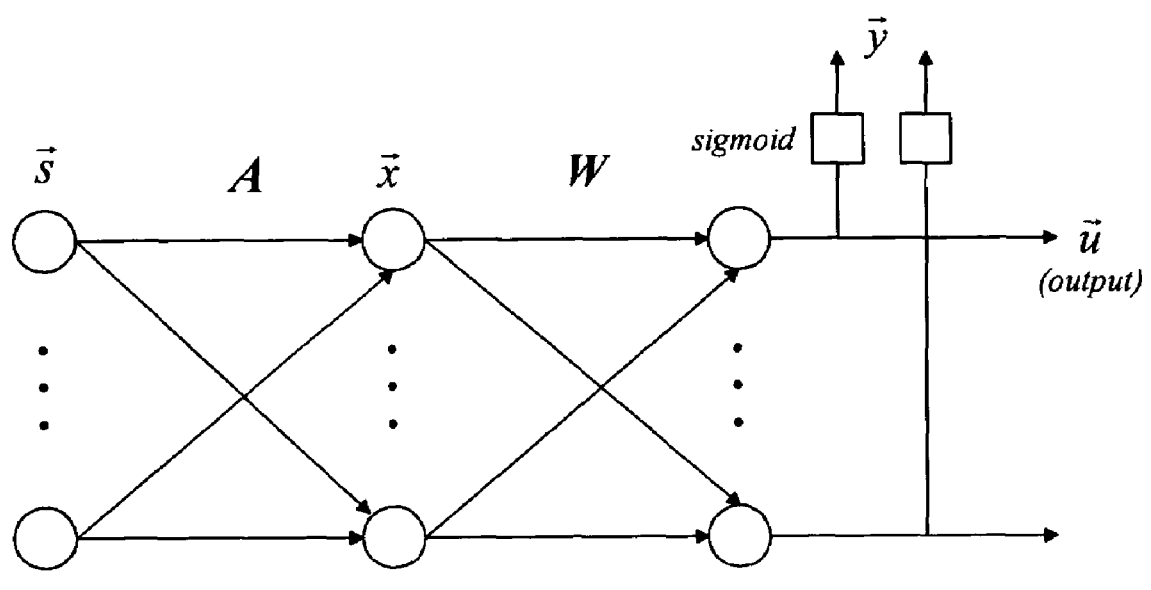
FIG. 1 is an illustration of the "BSAO", MaxEnt Neural Network 100 of the related art which implements natural gradient based unsupervised learning methodology searching for the post-processing weight matrix [W] by means of a typical contrast function: Maximum Entropy (MaxEnt) of integral version of the neuron's output.
Figure 2:
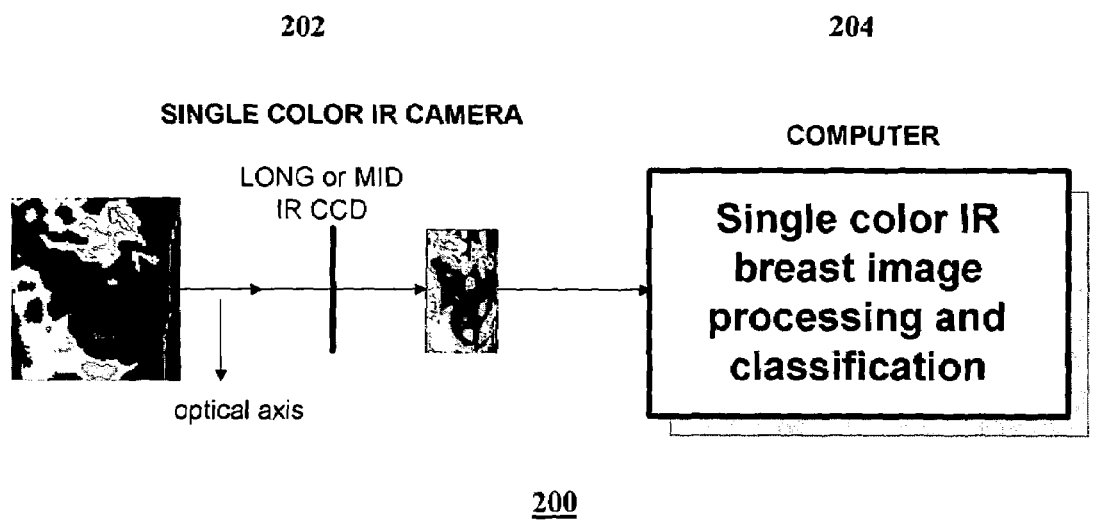
FIG. 2 shows a single color camera (short, mid or long IR) breast imaging 202 and processing 204 system of the related art.
Figure 3:
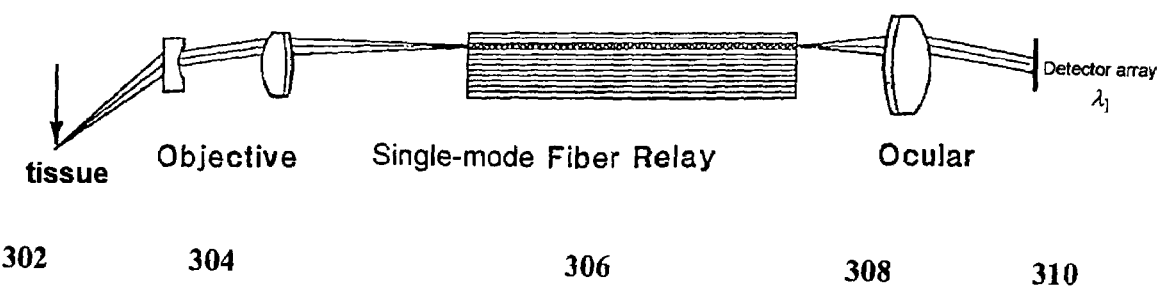
FIG. 3 is optical layout of a single-mode fiberoptic endoscope 300 of the related art. In the single-mode fiberoptic endoscope 300, light referenced from tissue 302 is directed by objective 304 into the single-mode fiber relay 306 to ocular lens 308 and detector array 301 which detects light of a single wavelength only.
Figure 4:
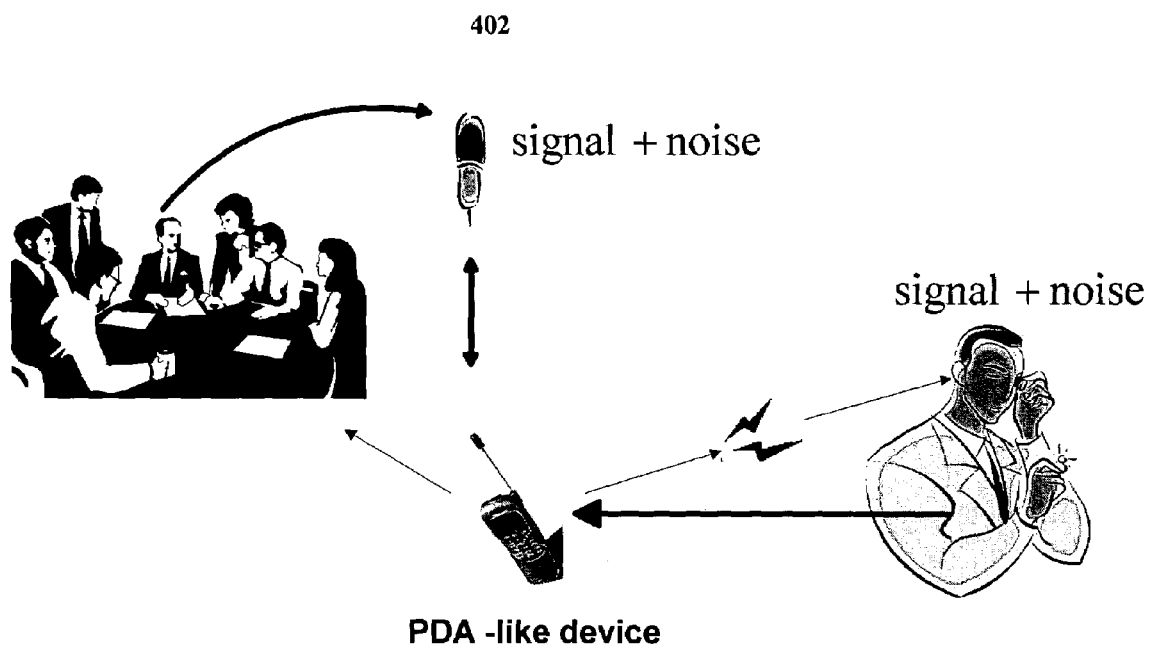
FIG. 4 is a single ear based selective amplification hearing system 400 of the related art, in which signal+noise is transmitted by detector 402 to a PDA-like device 404 which is transmitted to an earpiece 406. By using a single sensor (one ear) 402 system it becomes more difficult to cancel the noise or interference.

The single color camera system shown in FIG. 2 has been used so far to record IR breast imaging, ("Thermal Image Processing—Breast Cancer Detection Years Earlier," Alternative Medicine, pp. 29-35, September 1999; C. J. Wright, and C. B. Mueller, "Screening Mammography and Public Health Policy: The Need for Perspective," The Lancet 346 (July 1995), pp.29-32, and Ibid). IR breast images shown in FIG. 25, which shows long IR (8-12 µm) and FIG. 26, which shows mid IR (3-5 µm), are recorded in that way.

FIG. 25 shows a long IR (8-12 µm) image of the breasts 2500.

FIG. 26 shows a mid IR (3-5 µm) image of the breasts 2600.

The breast thermograms were taken of the same person, in the same room, under the same circumstances and with a medium wave (Cincinnati Electronics Iris 256 LN Indium Antimonide 3-5 µm) camera and a long wave (ICC, MBC 200 Platinum Selicide 9-12 µm) camera that were set as co-axially as physically possible. The patient that was the subject of the thermal imaging is a 47 year-old white female with a recent histologically confirmed diagnosis of stage 0/1 ductal carcinoma in situ (DCIS) in the cranial-lateral quadrant of the right breast.

Since IR cameras had different image formats and optical axis were impossible to make perfectly parallel it was obvious from FIGS. 25 and 26 that prior to applying the single pixel, non-linear blind de-multiplexing procedure (the LCNN blind de-mixing algorithm) of the present invention, a proper registration of the multi-modality breast images had to be done. The affine transform (H. H. Szu, "MO Imagery Techniques Using Arrays of Large Aperture Telescopes," Optics Communications, Vol. 32, No. 2, pp. 229-234, 1980; Map Tools in *ENVI User's Guide Version* 3.4, September 2000, Research Systems, Inc.) based image registration had been used for that purpose. The 2D affine transform between the point $\vec{P}$ on the reference image and point $\vec{P}'$ on the image to be registered was given with $\vec{P}' = A\vec{P} + \vec{T}$, where A is 2×2 area-preserving matrix and $\vec{T}$ is a translation vector. Thus, to register two images at least three reference points (2×2+2=6) should be identified on both images. Generally, registration error is smaller for smaller images. Moreover, the asymmetry is common between two breasts.

Therefore, the original images shown in FIGS. 25 and 26 had been segmented in two halves i.e. left breast and right breast images had been registered separately.

FIGS. 27A and 27B show the registered mid IR (2702, FIG. 27A, first component of the data vector X in models (3)/(22)) and long IR (2704, FIG. 27B, second component of the data vector X in models (3)/(22)) images of the right breast. White means high intensity. Image registration was necessary in order to overcome difficulties that come from using two different cameras with non-parallel optical axis and different size of the CCD sensors. That is, FIG. 27A and 27B show mid IR and long IR images, respectively, of the right breast after registration and histogram equalization.

The corresponding left breast images are shown in FIGS. 28A and 28B.

FIGS. 28A and 28B show the registered mid IR (2802, FIG. 28A, first component of the data vector X in models (3)/(22)) and long IR (2804, FIG. 28B, second component of the data vector X in models (3)/(22)) images of the left breast. White means high intensity. Image registration was necessary in order to overcome difficulties that come from using two different cameras with non-parallel optical axis and different size of the CCD sensors.

Vertical and horizontal labels represented pixel locations. It could be observed from all of FIGS. 27A, 27B, 28A, and 28B that nipples on both left and right breast on mid and long wave IR images are located at the practically same pixel locations. This is not the case with the original images shown in FIGS. 25 and 26.

A single axis two-color camera system of the present invention, shown in FIG. 22 and based on the single-pixel, non-linear blind de-mixing procedure of the present invention circumvents the difficulties which come from the use of single color and multiple optical axis cameras system. The single-pixel, non-linear blind de-mixing procedure of the present invention (the unsupervised LCNN algorithm) is applied to de-mixing of the sub-pixel spectral decomposition of the segmented and registered multispectral EO/IR breast images shown in FIGS. 27A, 27B, 28A, and 28B. Since the smart pixel processing of the single-pixel, non-linear blind de-mixing procedure of the present invention resolves sub-pixel spectral components with an unbiased and unsupervised learning ability it has been investigated whether the underlying independent texture feature could capture and tracked the pre-cancer anomaly heat generation or micro-calcification development.

FIGS. 29A and 29B show the LCNN de-mixed images 2902, first component of the source vector S in models (3)/(22), 2904, second component of the source vector S in models (3)/(22), of the right breast, de-mixed using the single pixel, non-linear de-mixing procedure of the present invention. White means class of high probability (1) and black means class of low probability (0). Independent classes represent healthy tissue since most large heat classes come from the inside of the breast.

FIGS. 30A and 30B show the LCNN de-mixed images 3002, first component of the source vector S in models (3)/(22), 3004, second component of the source vector S in models (3)/(22), of the left breast, de-mixed using the single pixel, non-linear de-mixing procedure of the present invention. White means class of high probability (1) and black means class of the low probability (0). The broken ring of small red pixel dots less than mili-meter size each and connected right outside quadrant, marked with the white circle, sharing the same texture of capillary shallow blood heat supply as the rest but should not be there since the nipple did not usually have the abnormal characteristics unless a stage zero ductal carcinoma in situ (DCIS).

That is, FIGS. 29A and 29B shows de-mixing results for the right breast while FIGS. 30A and 30B show de-mixing results for the left breast. In all of FIGS. 29A, 29B, 30A, and 30B, the white color means class of the high probability (close to 1), while black color means class of low probability (close to 0) i.e. practically absence of the class. The independent classes of the left breast shown in FIGS. 29A and 29B represent thermal classes of normal diffusive heat coming from large blood vessels since most large heat classes come from the blood vessels inside of the breast (Ch. Gorman, "Rethinking Breast Cancer," TIME, pp. 50-58, Feb. 18, 2002). The left breast de-mixed data into good and bad classes is shown in FIGS. 30A and 30B while the original data are shown in FIGS. 28A and 28B. The right upper half near the nipple, marked with the white circle, had a broken ring of small white pixel dots (less than mili-meter in size each and connected in the outside right quadrant) sharing the same texture of capillary shallow blood heat supply as the rest but they should not be there since the nipple does not usually have such an abnormal characteristics unless a stage zero ductal carcinoma in situ (DCIS). Left top is good thermal class (healthy tissue) because it represents a large heat class that comes from the inside of the chest. Unless DCIS exists the nipple does not usually has such characteristic (Ch. Gorman, "Rethinking Breast Cancer," TIME, pp. 50-58, Feb. 18, 2002), because the physiology of the breast suggests no existence of such heat sources around the normal healthy nipple.

According to (Ch. Gorman, "Rethinking Breast Cancer," TIME, pp. 50-58, Feb. 18, 2002) around 83% of the tumors were formed in the upper breast hemisphere. That gave strong indication that the mentioned right nipple surrounding region could be a DCIS. Tracking IR imaging history or histology would indicate whether DCIS were present. Following the same line of argumentation the left breast, shown in de-mixed independent classes in FIG. 18, could be considered to be healthy one since no such anomalies could be observed there. Here the texture representing blood heat supply comes all around the nipple without a break in the texture continuity.

The single-pixel, non-linear blind de-mixing algorithm of the present invention, based on the feedforward Lagrange Constraint Neural Network (LCNN) and multiple spectral data per pixel, increase the effectiveness of surveillance systems.

Thus, the present invention comprises features including:

1. a two-stage implementation of the single pixel, non-linear blind de-mixing procedure (the unsupervised nonlinear feedforward Lagrange Constraint Neural Network (LCNN) signal and image classification algorithm) according to Equations (1)-(52) and FIGS. 16 and 20 where in FIG. 20 first stage includes linearization or rectification and the second stage includes linear deterministic blind signal separation algorithm applied on linearized or rectified data vector assuming that the linearity condition $g(x_i)=x_i$ is satisfied.

2. the linear version of the single pixel, non-linear blind de-mixing procedure (the nonlinear feedforward LCCN algorithm) as in feature 1., according to the linearity condition $g(x_i)=x_i$ for unsupervised linear signal and image separation and classification as described by the Equations (1)-(52) the flow-chart diagram of which has been shown in FIG. 16.

3. implementation of the linear or non-linear version of the single pixel, non-linear blind de-mixing procedure (non-linear or linear feedforward LCNN algorithm) as in features 1. and 2. in a scalable way on analog and mixed (analog and digital) VLSI circuits based on the design shown in FIGS. 16, 17, 18, and 19 and an example of such scalable solution for 0.25 micrometer VLSI implementation shown in FIG. 21.

4. implementation of the single pixel, non-linear blind de-mixing procedure as an unsupervised nonlinear signal and image separation and classification algorithm coined Lagrange Constraint Neural Network (feedforward LCNN) as described by equations (1)-(52) and in features 1 and 2 on a digital signal processor (DSP) or Field Programmable Gate Arrays (FPGA) in accordance with the flow-chart diagram shown in FIG. 16.

5. a two-camera single optical axis based IR imaging system such as shown in FIG. 22.

6. early breast pre-cancer ductal carcinoma in situ tumor classification, diagnosis and tracking by using multiple camera sensory system as discussed in feature 5 and the single pixel, non-linear blind de-mixing procedure as a smart unsupervised feedforward LCNN algorithm as discussed in features 1, 2, 3, and 4.

7. tracking IR imaging history or histology by using a two-camera single optical axis based sensory system as discussed in feature 5 and the single pixel, non-linear blind de-mixing procedure as a smart unsupervised LCNN algorithm as discussed in features 1, 2, 3, and 5 in a way as discussed in feature 6.

8. in situ fiberoptical data gathering by means of a multiple mode fiberoptic recording as shown in FIG. 21 and the single pixel, non-linear blind de-mixing procedure as a smart unsupervised feedforward LCNN algorithm for image processing and classification as discussed in features 1, 2, 3, and 4.

9. passive detection of blockages in the human body fluid circulatory system using the single pixel, non-linear blind de-mixing procedure as an unsupervised LCNN algorithm as discussed in features 1, 2, 3, and 4 and multiple sensors based imagining and diagnostic equipment as discussed in features 5, 6, 7, and 8 and infrared imaging as well as to passively detect blockages in the body fluid circulatory system that might be of importance for coronary artery bypass surgery, diabetes, and deep vein thrombosis.

10. passive detection and diagnosis of rheumatic arthritis by means of two-camera single optical axis based sensory system as discussed in feature 5., and the single pixel, non-linear blind de-mixing procedure as a smart unsupervised feedforward LCNN algorithm as discussed in features 1., 2, 3, and 4.

11. selective amplification hearing aids through de-noise echo cancellation and signal classification simultaneously by means of two-ear binaural processing as shown in FIG. 24 and based on the single pixel, non-linear blind de-mixing procedure as an unsupervised nonlinear or linear feedforward LCNN algorithm as discussed in features 1., 2., 3., and 4.

In addition, the single pixel, non-linear blind de-mixing procedure of the present invention can be used to enable a digital local thermometer to detect early pre-cancer in a home-screening environment using a single camera in which an exposure is taken of a particular body area, the film used is electric film (such as a charge coupled device (CCD)) and is placed in electronic or freon cooling (refrigeration) overnight, and a second exposure of the same body area is taken using the same camera and the same film the next day. Multiple wavelengths (including middle IR (3-5 micrometers) and long IR (8-12 micrometers) are used, and the film is cryogenically cooled. Temporal integration is applied, such that the sequence is picture, cooling, picture again the next day, thus eliminating thermal noise (Brownian motion noise).

In addition, the Fast Simulated Annealing algorithm by H. Szu is used to seek the global minimum of Helmholtz Free energy of the isothermal system.

The present invention measures multiple radiation components forming a data vector per single pixel $X=(X_1, X_2, \ldots)$ in order to determine uniquely the underlying sources forming a source vector $S=(S_1, S_2, \ldots)$ propagating through a nonlinear mixing medium. The present invention adopts that the thermal diffusion is constrained isothermally at the equilibrium free energy, known as Helmholtz free energy: $H=E-TS$ where E is the energy, T is the equilibrium reservoir temperature and S denotes the classical Shannon information theory entropy In this sense, the present invention generalizes the classical Shannon information theory, which states the special case of a closed system $E=0$ and the entropy must be evolving toward the maximum for the absolute equilibrium. The present invention postulates the state of an open equilibrium system defined by the feedforward first order error energy $E(X/S)=\mu\{g([W]X)-S\}$ which can be reduced to the second order Least Mean Square (LMS) error energy for a specific Lagrange constraint vector $\mu$. The present invention seeks among all possible vector sources $S=(S_1, S_2, \ldots)$ the one that satisfies the minimum H for arbitrary mixing matrix [A] and smooth nonlinearity $g:X=g^{-1}\{[A]S\}$. This physical condition of isothermal equilibrium is a strong constraint which permits the present invention to invert the single-pixel data blindly for S, without knowing ahead the mixing matrix and nonlinearity.

Moreover, the practice of this patent has demonstrated the possibility of an early malign tumor detection by taking two pictures using two spectral cameras non-intrusively. Each pair of input pixel data vector has two components, a long wavelength (8-12 micrometer) and a middle wavelength (3-5 micrometer). Such a pair per pixel is defined as a vector $X(pixel, t)=(X_{long}(pixel, t), X_{short}(pixel, t))$, where t indicates a repetition time that can reveal the growth of a malign tumor which is usually mixed with a benign one in terms of a unknown percentage source vector $S(pixel, t)=(S_{benign}(pixel, t), S_{malign}(pixel, t))$. This expectation is realistic because the physics of radiation source indicates a shift toward a shorter wavelength spectrum $X_{short}(pixel, t)$ associated with the massive nutrition feed of a warmer lymph and blood toward a rapid growth of a malign tumor (biologically known as the Angiogenesis property). Then, the quantitative value of the malign tumor source $s_{malign}/(s_{malign}+S_{benign})$ can be determined by imposing the generalized information theory at a local equilibrium in terms of the Helmholtz free energy.

The present invention furthermore generalizes the physical demixing system to include brain-like unsupervised learning artificial neural networks. The present invention observes that input pairs (e.g. two eyes $X_1$ and $X_2$) can stimulate the binding of otherwise random brain waves which must diffuse to make room and save the energy E at an isothermal reservoir brain-temperature T (known as the cybernetic temperature of biological homeostasis theory).

The system also includes permanent or removable storage, such as magnetic and optical discs, RAM, ROM, etc. on which the process and data structures of the present invention can be stored and distributed. The processes can also be distributed via, for example, downloading over a network such as the Internet.

The many features and advantages of the invention are apparent from the detailed specification and, thus, it is intended by the appended claims to cover all such features and advantages of the invention that fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

What is claimed is:

1. A method of early breast pre-cancer ductal carcinoma in situ tumor classification, diagnosis and tracking using a digital heat spectrum local thermometer, by determining uniquely underlying sources forming a source vector $S=(S_1, S_2, \ldots)$ propagating through a nonlinear mixing medium of a constant temperature, open equilibrium system by measuring multiple radiation components forming a data vector per single pixel $X=(X_1, X_2, \ldots)$ comprising:

receiving, by a multispectral infrared (IR) camera of the digital heat spectrum local thermometer, a beam of the data vector X of spectral data including data corresponding to a passive heat source, splitting the beam into a mid IR beam and a long IR beam, converting by a first charge-coupled device the long IR beam into a first image, and converting by a second charge-coupled device the mid IR beam into a second image;

receiving, by a computer of the digital heat spectrum local thermometer, the first image and the second image, cooling the first charge-coupled device and the second charge-coupled device;

receiving, by the multispectral infrared (IR) camera, a second beam of data vector of spectral data including data corresponding to the heat source, splitting the second beam into a second mid IR beam and a second long IR beam, converting by the first charge-coupled device the second long IR beam into a third image, and converting by the second charge-coupled device the mid IR beam into a fourth image;

applying, by the computer, a constraint to the equilibrium system such that the thermal diffusion of the equilibrium system is constrained isothermally at the equilibrium free energy, wherein the equilibrium free energy is the Helmholtz free energy $H=E-TS$, wherein E is the energy, T is the equilibrium reservoir temperature, and S is the classical Shannon information theory entropy, defining a state of the open equilibrium system by a feed-forward first order error energy $E(X/S)=\mu\{g([W]X)-S\}$, wherein $\mu$ is the Lagrange constraint vector and [W] is the feed-forward matrix, reducing the feed-forward first order energy $E(X/S)$ to a second order Least Mean Square (LMS) error energy for a specific Lagrange constraint vector $\mu$, and determining from among all possible vector sources $S=(S_1, S_2, \ldots)$ one vector source that satisfies the minimum H for an arbitrary mixing matrix [A] and smooth nonlinearity g: $X=g^{-1}\{[A]S\}$, wherein [A] is the heat transport mixing matrix and is the inverse of [W]; and providing the one vector source corresponding to the minimum H.

2. A method of early breast pre-cancer ductal carcinoma in situ tumor classification, diagnosis and tracking comprising:

receiving, by a multispectral infrared (IR) camera on a single optical axis, a beam of data vector of spectral data including data corresponding to a passive heat source, splitting the beam into a mid IR beam and a long IR beam, converting the long IR beam into a first image, and converting the mid IR beam into a second image;

receiving, by a computer, the first image and the second image, and executing a single pixel, non-liner blind de-mixing procedure as a nonlinear Lagrange Constraint Neural Network unsupervised two-spectral IR breast image classification on the first image and the second image to determine a temperature of the heat source; and providing the temperature of the heat source for tumor classification, diagnosis and tracking.

3. A method of early breast pre-cancer ductal carcinoma in situ tumor classification, diagnosis and tracking using a digital heat spectrum local thermometer comprising:

receiving, by a multispeetral infrared (IR) camera of the digital heat spectrum local thermometer, a bean of data vector of spectral data including data corresponding to a passive heat source, splitting the beam into a mid IR beam and a long IR beam, converting by a first charge-coupled device the long IR beam into a first image, and converting by a second charge-coupled device the mid IR beam into a second image;

receiving, by a computer of the digital heat spectrum local thermometer, the first image and the second image, cooling the first charge-coupled device and the second charge-coupled device;

receiving, by the multispectral infrared (IR) camera, a second beam of data vector of spectral data including data corresponding to the heat source, splitting the second beam into a second mid IR beam and a second long IR beam, converting by the first charge-coupled device the second long IR beam into a third image, and converting by the second charge-coupled device the mid IR beam into a fourth image;

executing, by the computer, a single pixel, non-linear blind de-mixing procedure as a nonlinear Lagrange Constraint Neural Network unsupervised two-spectral IR breast image classification on the first image, the second image, the third image, and the fourth image to determine a termperature of the heat source; and providing the temperature of the heat source for tumor classification, diagnosis and tracking.

4. A method of tracking infrared imaging history or histology, comprising:

receiving, by a multispectral infrared (IR) camera on a single optical axis, a beam of data vector of spectral data including data corresponding to a passive heat source, splitting the beam into a mid IR beam and a long IR beam, converting the long IR beam into a first image, and converting the mid IR beam into a second image;

receiving, by a computer, the first image and the second image, and executing a single pixel, non-linear blind de-mixing procedure as a nonlinear Lagrange Constraint Neural Network unsupervised two-spectral IR breast image classification on the first image and the second image to determine a temperature of the heat source; and providing the temperature of the heat source for tumor classification, diagnosis and tracking.

5. A method of in situ data gathering by a multiple mode fiberoptic recording, comprising:

receiving, by an objective lens, a beam of multiple wavelengths and including a data vector of spectral data including data corresponding to a passive heat source of a tissue image;

transmitting, by the objective lens, the beam to a dual-mode fiber relay;

receiving, by an ocular lens, the beam passing through the dual-mode fiber relay;

focusing, by the ocular lens, the beam on a scanning mirror;

reflecting, by the scanning mirror, a first wavelength of the beam onto a first detector array, and a second wavelength of the beam onto a second detector array;

de-mixing a first tissue image and a second tissue image by a computer executing a single pixel, non-linear blind de-mixing procedure as a nonlinear Lagrange Constraint Neural Network unsupervised two-spectral image classification procedure;

de-mixing a tissues image corresponding with virtual tumor artificially introduced by molecular tagging of fluorescence proteins; and providing the tissues image.

6. A method of passive detection of blockages in the body fluid circulatory system comprising:

receiving, by a multispectral infrared (IR) camera on a single optical axis, a beam of data vector of spectral data including data corresponding to a heat source, splitting the beam into a mid IR beam and a long IR beam, converting the long IR beam into a first image, and converting the mid IR beam into a second image; and receiving, by a computer, the first image and the second image, and executing a single pixel, non-linear blind de-mixing procedure as a nonlinear Lagrange Constraint Neural Network unsupervised two-spectral IR image classification on the first image and the second image to determine a temperature of the heat source; and providing the temperature of the heat source for passive detection of blockages.

7. The method of claim 6, wherein the detected blockages are in the coronary arteries.

8. The method of claim 6, wherein the detected blockages are deep vein thrombosis.

9. The method of claim 6, wherein the detected blockages relate to diabetes.

10. A method of passive detection and diagnosis of rheumatic arthritis comprising:

receiving, by a multispectral infrared (IR) camera on a single optical axis, a beam of data vector of spectral data including data corresponding to a heat source, splitting the beam into a mid IR beam and a long IR beam, converting the long IR beam into a first image, and converting the mid IR beam into a second image; and receiving, by a computer, the first image and the second image, and executing a single pixel, non-linear blind de-mixing procedure as a nonlinear Lagrange Constraint Neural Network unsupervised two-spectral IR image classification on the first image and the second image to determine a temperature of the heat source; and providing the temperature of the heat source for detection of rheumatic arthritis.

* * * * *